(12) United States Patent
Grimm et al.

(10) Patent No.: US 9,913,690 B2
(45) Date of Patent: Mar. 13, 2018

(54) SYSTEM AND METHOD FOR PRE-OPERATIVELY DETERMINING DESIRED ALIGNMENT OF A KNEE JOINT

(75) Inventors: James Grimm, Winona Lake, IN (US); Anthony Romano, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 1137 days.

(21) Appl. No.: 13/333,505

(22) Filed: Dec. 21, 2011

(65) Prior Publication Data

US 2013/0166254 A1  Jun. 27, 2013

(51) Int. Cl.
| | |
|---|---|
| G06F 17/50 | (2006.01) |
| A61B 34/10 | (2016.01) |
| G06F 19/00 | (2018.01) |
| A61B 17/17 | (2006.01) |

(52) U.S. Cl.
CPC .............. *A61B 34/10* (2016.02); *G06F 17/50* (2013.01); *A61B 17/1764* (2013.01); *A61B 2034/104* (2016.02); *A61B 2034/105* (2016.02); *G06F 17/5009* (2013.01); *G06F 19/3437* (2013.01)

(58) Field of Classification Search
None
See application file for complete search history.

(56) References Cited

U.S. PATENT DOCUMENTS

| | | | |
|---|---|---|---|
| 5,871,018 A * | 2/1999 | Delp et al. ..................... 128/898 |
| 7,981,158 B2 | 7/2011 | Fitz et al. | |
| 9,358,114 B2 * | 6/2016 | Hughes ................ A61B 17/157 |
| 2005/0113846 A1 | 5/2005 | Carson | |
| 2005/0256389 A1 | 11/2005 | Koga et al. | |
| 2006/0004284 A1 | 1/2006 | Grunschlager et al. | |
| 2007/0015995 A1 * | 1/2007 | Lang et al. .................... 600/407 |
| 2007/0066917 A1 * | 3/2007 | Hodorek et al. ............. 600/595 |
| 2009/0270868 A1 * | 10/2009 | Park et al. ...................... 606/87 |
| 2010/0256479 A1 | 10/2010 | Park et al. | |
| 2010/0261998 A1 * | 10/2010 | Stiehl ............................ 600/424 |
| 2011/0282473 A1 * | 11/2011 | Pavlovskaia et al. .......... 700/98 |
| 2011/0305379 A1 * | 12/2011 | Mahfouz ....................... 382/131 |

(Continued)

FOREIGN PATENT DOCUMENTS

WO  WO-2013095716 A1  6/2013

OTHER PUBLICATIONS

Freeman, et al., ". . . The movement of the normal tibio-femoral joint," Journal of Biomechanics, vol. 38, 2005, pp. 197-208.*
Churchill, L., et al., "The Transepicondylar Axis Approximates the Optimal Flexion Axis of the Knee," Clinical Orthopaedics and Related Research, No. 356, 1998, pp. 111-118.*

(Continued)

*Primary Examiner* — Aniss Chad
*Assistant Examiner* — David M Rogers
(74) *Attorney, Agent, or Firm* — Schwegman Lundberg & Woessner, P.A.

(57) ABSTRACT

A joint alignment method comprises using imaging data of at least a portion of a leg to create a leg model, wherein the leg model includes a femur having medial and lateral condyles and a tibia having tibial plateaus that are configured to engage the medial and lateral condyles at a knee joint, displaying an image of the leg model for manipulation by a user, locating a pivot point within one of the medial or lateral condyles, and rotating, in the displayed image, the tibia with respect to the femur, about the pivot point, to obtain a desired knee joint articulation in a specified plane.

14 Claims, 25 Drawing Sheets

(56) References Cited

U.S. PATENT DOCUMENTS

2012/0330367 A1* 12/2012 Roche et al. ............... 606/86 R

OTHER PUBLICATIONS

Hollister, A., et al., "The Axes of Rotation of the Knee," Clinical Orthopaedics and Related Research, No. 290, 1993, pp. 259-268.*
Most, E., et al., "Sensitivity of the Knee Joint Kinematics Calculation to Selection of Flexion Axes," Journal of Biomechanics, No. 37, 2004, pp. 1743-1748.*
Asano, T., et al., "In Vivo Three-Dimensional Knee Kinematics Using a Biplanar Image-Matching Technique" Clinical Orthopaedics and Related Research, No. 388, 2001, pp. 157-166.*
Schwartz, M. et al., "A New Method for Estimating Joint Parameters From Motion Data," Journal of Biomechanics, No. 38, 2005, pp. 107-116.*
"International Application Serial No. PCT/US2012/049117, International Preliminary Report on Patentability mailed Jul. 3, 2014", 7 pgs.
"International Application Serial No. PCT/US2012/049117, International Search Report and Written Opinion Mail Nov. 2, 2012", Partial Document—Checked WIPO full document wasn't available Mar. 27, 2014, 4 pg.
"European Application Serial No. 12746216.6, Communication Pursuant to Article 94(3) EPC mailed Sep. 30, 2015", 4 pgs.
"European Application Serial No. 12746216.6, Response filed Apr. 18, 2016 to Communication Pursuant to Article 94(3) EPC mailed Sep. 30, 2015", 11 pgs.
"European Application Serial No. 12746216.6, Communication pursuant to Article 94(3) EPC mailed Jul. 22, 2016", 4 pgs.
"European Application Serial No. 12746216.6, Response filed Mar. 16, 2015 to Communication pursuant to Rules 161(1) and 162 EPC mailed Sep. 5, 2014", 8 pgs.
"European Application Serial No. 12746216.6, Communication Pursuant to Article 94(3) EPC dated Mar. 10, 2017", 4 pgs.
"European Application Serial No. 12746216.6, Response filed Dec. 1, 2016 to Communication Pursuant to Article 94(3) EPC dated Jul. 22, 2016", 8 pgs.

* cited by examiner

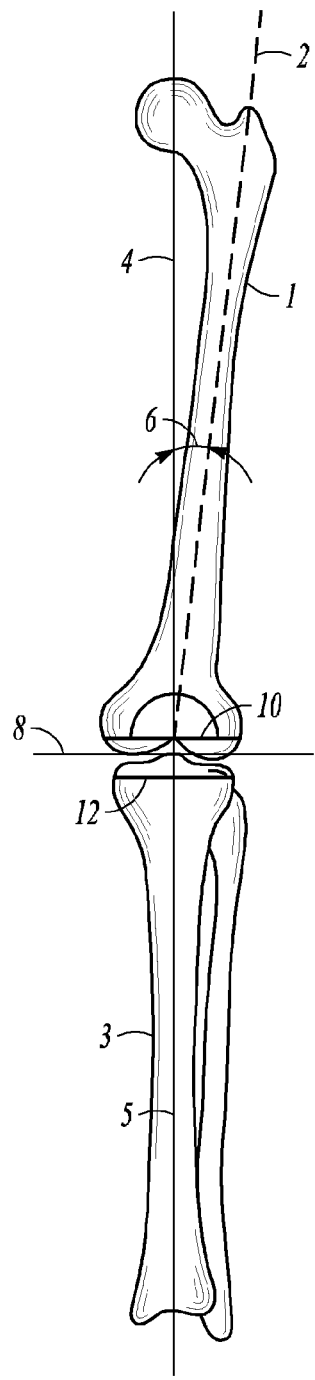
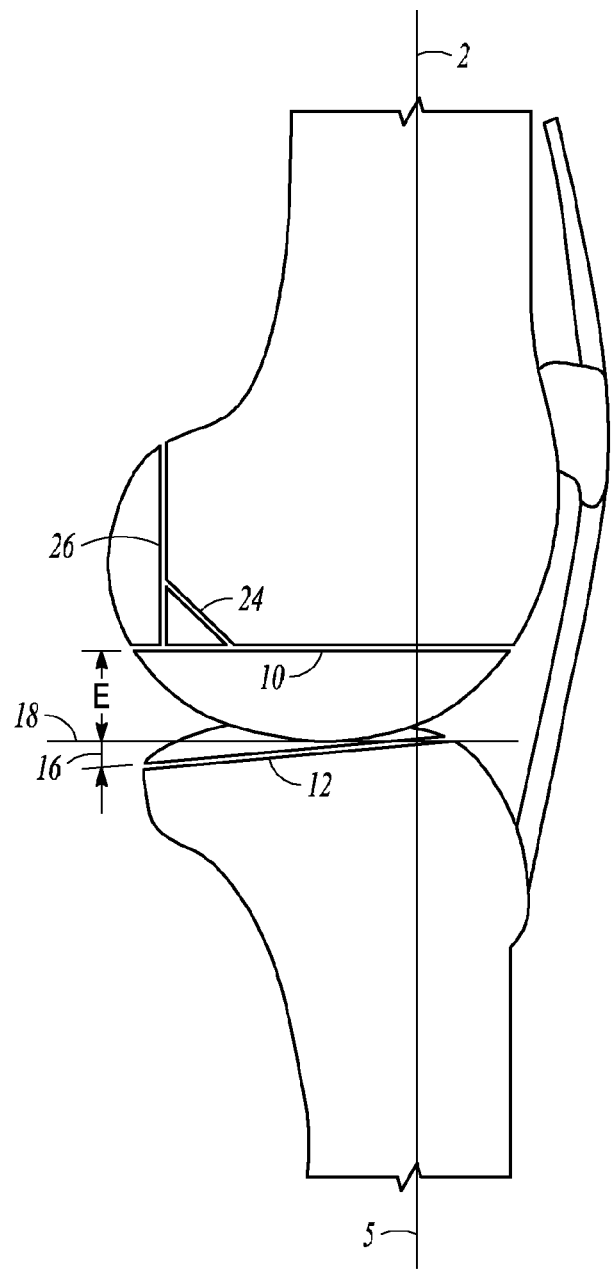
FIG. 1
FIG. 2

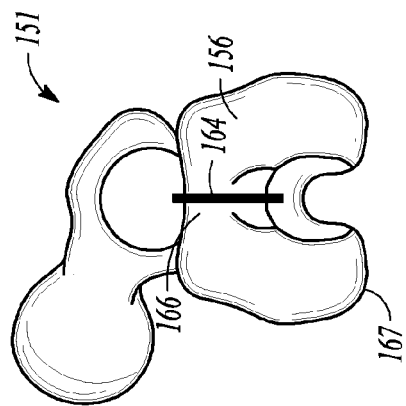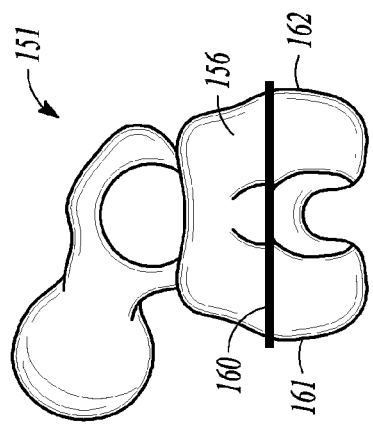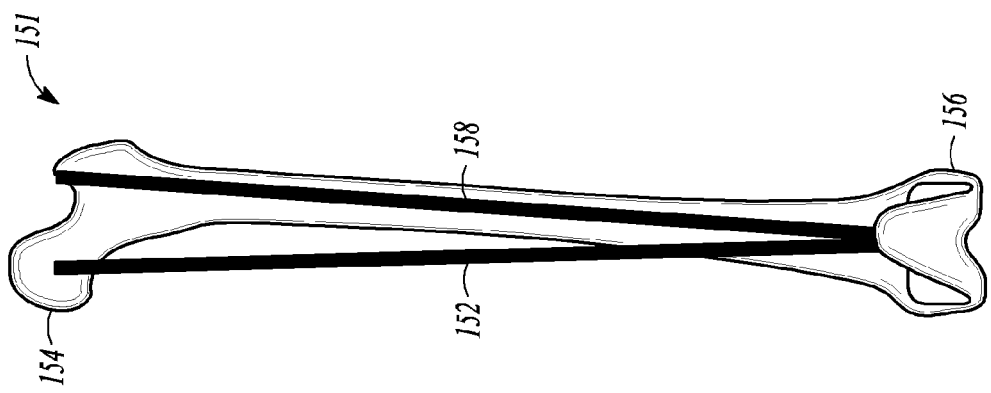

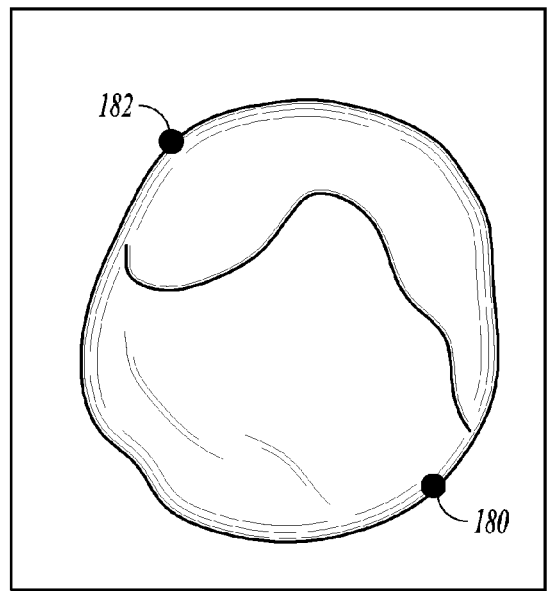
FIG. 18A
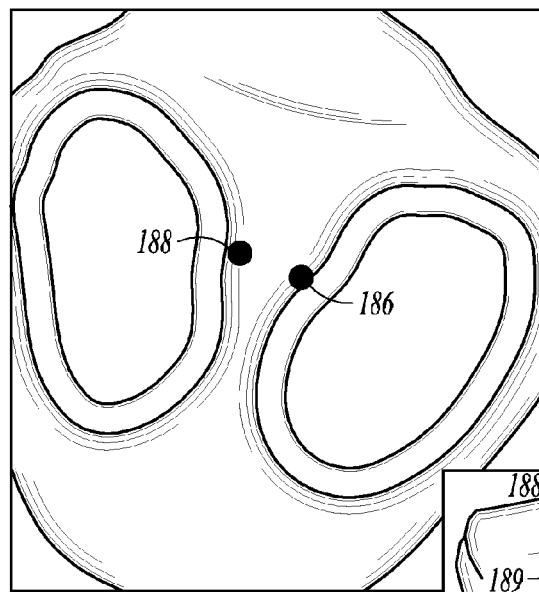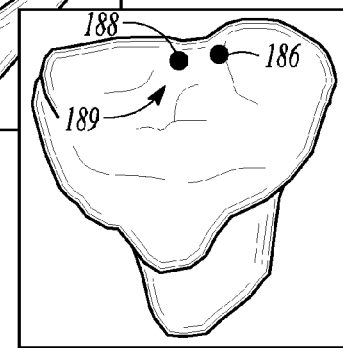
FIG. 18B

SYSTEM AND METHOD FOR PRE-OPERATIVELY DETERMINING DESIRED ALIGNMENT OF A KNEE JOINT

TECHNICAL FIELD

The present patent application relates to unicondylar knee arthroplasty, and, more particularly, to a method for achieving a desired joint alignment during a knee replacement procedure.

BACKGROUND

Orthopedic procedures for the replacement of all, or a portion of, a patient's joint have been developed over the last thirty years. Currently, the procedures used to prepare the bone and seat the implants are generally referred to as open procedures. For the purposes of this discussion, the term "open procedure" will refer to a procedure wherein an incision is made through the skin and underlying tissue to fully expose a large portion of the particular joint surface. In both total and unicondylar knee arthroplasty, the typical incision for an open procedure can be about 7-12 inches long. After the initial incision in the skin, the internal wound can be enlarged to fully expose the areas to be prepared. While this approach provides surgeons with an excellent view of the bone surface, the underlying damage to the soft tissue, including the muscles, can lengthen a patient's rehabilitation time after surgery. While the implants may be well fixed at the time of surgery, it may be several weeks or perhaps months before the tissues violated during surgery are fully healed.

Unicompartmental knee arthroplasty can be utilized to correct a varus or a valgus deformity caused by, e.g., osteoarthritis affecting the medial (a varus deformity) or lateral (a valgus deformity) compartment of the knee. Traditionally, unicondylar knee arthroplasty is an open procedure in which a surgeon, after exposing the knee, resects diseased or otherwise undesirable bone from the appropriate compartment of the knee, including portions of the distal femur and the proximal tibia. The distal femur and proximal tibia of the affected compartment are also shaped to receive a unicondylar knee prosthesis.

In traditional unicondylar knee arthroplasty, leg alignment requires a trial and error technique in which the surgeon makes a distal femoral cut and a proximal tibial cut and thereafter selects the location of the other of the distal femoral cut and the proximal tibial cut based on experience and the knowledge that tibial prostheses are available in a limited number of thicknesses. Typically, the proximal tibial cut is made so as to remove the least amount of the proximal tibia, while ensuring sufficient removal of diseased or otherwise undesirable bone. The remaining femoral cuts can be made to complete shaping of the femur to receive a femoral prosthesis. After the femoral and tibial cuts are complete, the femoral prosthesis and the tibial prosthesis, or provisional versions thereof, can be temporarily implanted and leg alignment reviewed by the surgeon. If the tibial prosthesis does not include an integral bearing component, then a discrete bearing component can also be implanted. To adjust alignment of the leg, the surgeon can replace the tibial prosthesis or bearing component with an alternative tibial prosthesis or bearing component having an increased or decreased thickness. The surgeon can also recut the femur to achieve appropriate alignment. Additionally or alternatively, the surgeon can remove more tibial bone stock and again insert the previously used tibial prosthesis, or replace the previously used tibial prosthesis with a tibial prosthesis of a different thickness. This procedure of trial and error can be conducted until the surgeon believes that the appropriate alignment has been achieved.

Overview

This overview is intended to provide an overview of subject matter of the present patent application. It is not intended to provide an exclusive or exhaustive explanation of the invention. The detailed description is included to provide further information about the present patent application.

The present inventors have recognized, among other things, that the traditional trial and error technique utilized in performing unicompartmental knee arthroplasty is tedious and time consuming, and could result in excessive removal of tibial and/or femoral bone. Thus, the present inventors have recognized that what is needed in the art is a system and method for visualizing joint alignment that allows the surgeon to pre-operatively visualize and identify a desirable alignment of the knee joint. Providing such pre-operative planning means can greatly reduce the amount of time necessary for a surgeon to select the appropriate prosthesis components, as well as the amount of unnecessary bone that is removed from the tibia and/or femur.

In an example a joint alignment method is provided that includes using imaging data of at least a portion of a leg to create a leg model, wherein the leg model includes a femur having medial and lateral condyles and a tibia having tibial plateaus that are configured to engage the medial and lateral condyles at a knee joint, displaying an image of the leg model for manipulation by a user, locating a pivot point within one of the medial or lateral condyles, and rotating, in the displayed image, the tibia with respect to the femur, about the pivot point, to obtain a desired knee joint articulation in a specified plane. The leg model can be a three-dimensional model that is created using two or more two-dimensional images of the leg.

In an example a pre-operative method for visualizing alignment of a joint is provided that includes displaying a three-dimensional model of a knee joint, wherein the three-dimensional model includes a distal end of a femur having an arthritic condyle and a non-arthritic condyle and a proximal end of a tibia having a tibial plateau, locating a pivot point within the non-arthritic condyle, wherein the pivot point is located at a center of an arc that approximates a curvature of an articulation surface of the non-arthritic condyle, and manipulating the displayed position of the arthritic condyle by rotating the tibia about the pivot point.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is a front elevation view of a tibia and a femur showing axes of a knee joint.

FIG. 2 is a side section view of a knee joint showing typical bone cuts used in replacing joint surfaces.

FIGS. 15A-15C are diagrams of a three-dimensional femur illustrating various axes derived from the femoral anatomical reference points.

FIGS. 18A and 18B are diagrams illustrating exemplary images that can be presented for selecting anatomical reference points associated with a tibia.

DETAILED DESCRIPTION

The present patent application relates to systems and methods for determining a desired joint alignment during a knee arthroplasty procedure. During a typical arthroplasty procedure, an incision is made into the knee joint to expose the bones comprising the joint. Cutting guides can then be used to guide the removal of the articular surfaces that are to be replaced. In order to help the surgeon decide upon the appropriate resection locations on the bone ends, as well as the appropriate artificial joint components for replacing the resected bone ends, a pre-operative planning system can be used to generate an image of the joint and allow the surgeon to plan the procedure in a virtual environment prior to making an incision in the patient.

Figure 3:
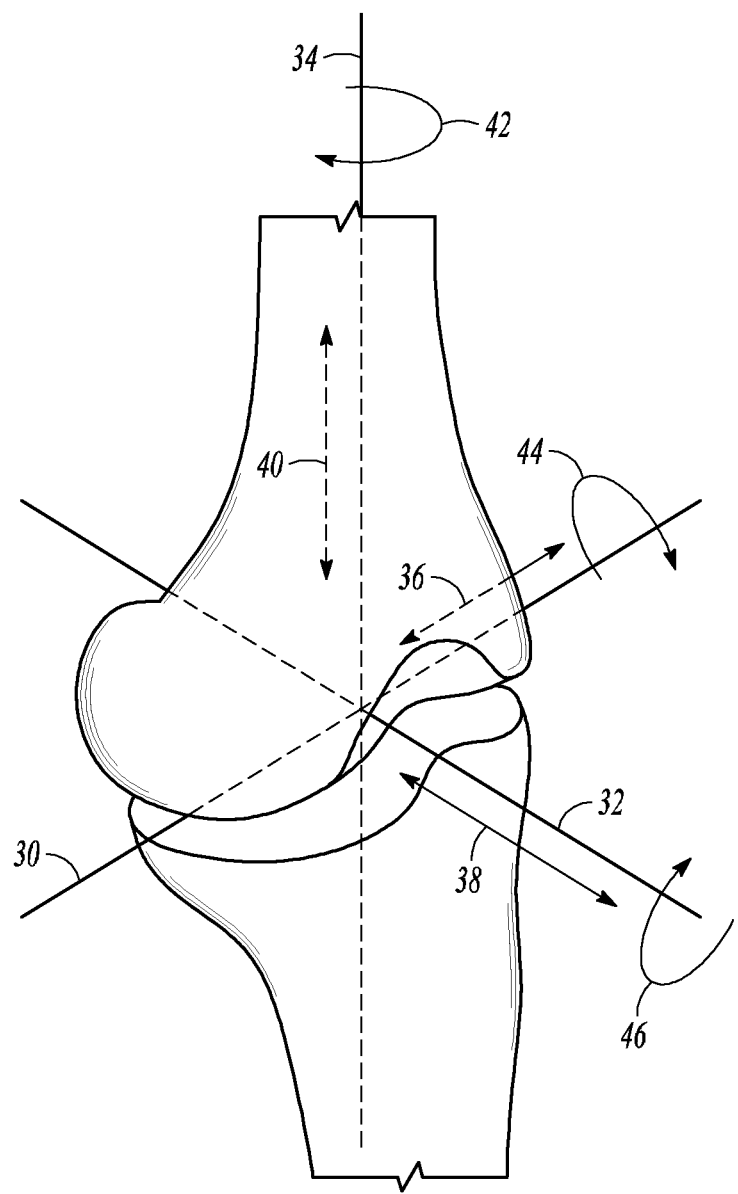
FIG. 3 is a perspective view of a knee joint showing aspects of component positioning.

In order to better understand knee arthroplasty procedures, it is helpful to understand the relationship of the bones and the cuts made to orient the various implant components. FIGS. 1-3 illustrate several aspects of implant orientation. Beginning with FIG. 1, a diagram of the lower limb in the frontal plane is presented to illustrate various axes of the lower limb. For example, the femur 1 has an anatomic axis 2 coinciding generally with its intramedullary canal. The femur 1 also has a mechanical axis 4, or load axis, running from the center of the femoral head to the center of the knee. The angle 6 between these two axes varies within the patient population but is generally on the order of 6 degrees. Likewise, the tibia 3 has an anatomic axis coinciding generally with its intramedullary canal. The mechanical axis 5 of the tibia 3 runs from the center of the knee to the center of the ankle and is generally collinear with the anatomic axis. The transverse axis, or joint line 8, about which the knee flexes, is parallel to a line through the medial and lateral femoral condyles and parallel to the tibial plateau. Although illustrated as perpendicular in FIG. 1, in an example, this line can subtend a slight valgus angle of approximately 87 degrees with the mechanical axis 4 of the femur 1 and a slight varus angle of approximately 87 degrees with the mechanical axis 5 of the tibia 3. Thus, the distal femur is in slight valgus and the proximal tibia is in slight varus. Normally, portions of the distal femur and proximal tibia are resected to be parallel to the joint line 8, and thus perpendicular to the mechanical axis 4, as indicated at 10 and 12. The intersection of the femoral and tibial mechanical axes, 4 and 5, can subtend an angle relative to one another. However, the angle is small and the mechanical axis 4 of the femur 1 has an approximately normal alignment with the proximal tibia if the knee is uninjured.

FIG. 2 illustrates the knee joint from the side or sagittal view and various bone cuts that can be made to align implant components. The distal femur can be cut 10 perpendicular, in the anterior-to-posterior direction, to the anatomic axis 2 of the femur. The proximal tibial resection 12 can be cut to match the natural posterior slope of the proximal tibia relative to the tibial mechanical axis 5. The amount of posterior slope 16 relative to a reference line 18 perpendicular to the tibial mechanical axis 5 varies in the patient population but is typically on the order of about 5 degrees. The distance between the distal femoral 10 and proximal tibial 12 cuts along the mechanical axes 4 and 5 is the extension gap E. Other cuts can be made depending on the components that are to be implanted. These can include a posterior femoral chamfer cut 24, and a posterior femoral cut 26. Additional preparation of the bone can include drilling or notching the bones to receive pegs, stems, and other extensions from the components (not shown).

FIG. 3 depicts six aspects of component positioning relative to a coordinate system in which the x-axis 30 corresponds approximately to the joint line 8, the z-axis 34 corresponds approximately to the mechanical axes 4 and 5, and the y-axis 32 is normal to the other two. Position along each of these axes is depicted by arrows. Particularly, position along the x-, y-, and z-axes determines the medial/lateral (dx) 36, anterior/posterior (dy) 38, and proximal/distal (dz) 40 positioning of components, respectively. Rotation about each of these axes is also depicted by arrows. Rotation about the z-axis (rz) 42 corresponds anatomically to external rotation of the femoral component, while rotation about the x-axis (rx) 44 and y-axis (ry) 46 corresponds to extension plane slope and varus/valgus angle, respectively.

Depending on the order of the cuts, and the way that subsequent instruments reference each cut, the position of the distal femoral cut 10 can affect the location of the joint line (dz), the extension gap, the varus/valgus angle (ry), and the extension plane angle (rx). Likewise, the position of the proximal tibial cut 12 can affect the varus/valgus angle (ry), extension plane (rx), external rotation (rz), and the joint line (dz) or extension gap.

Figure 6:
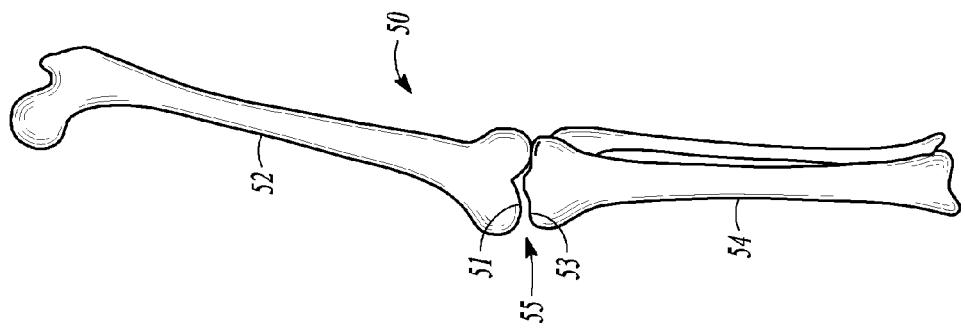
FIGS. 4, 5, and 6 are front elevation views illustrating a knee joint with normal or neutral pre-surgical joint alignment, varus pre-surgical joint alignment, and valgus pre-surgical joint alignment, respectively.
Figure 5:
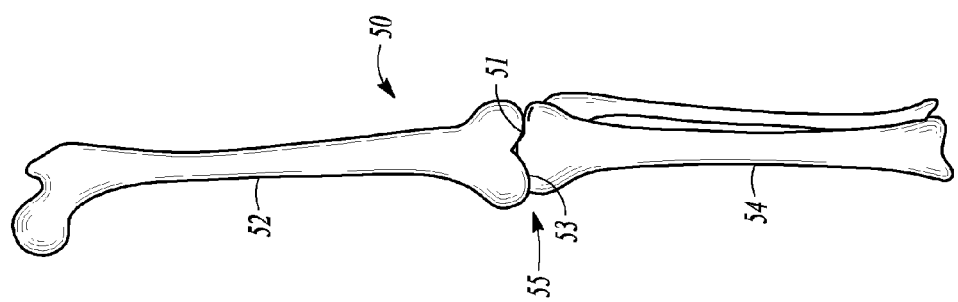
Figure 4:
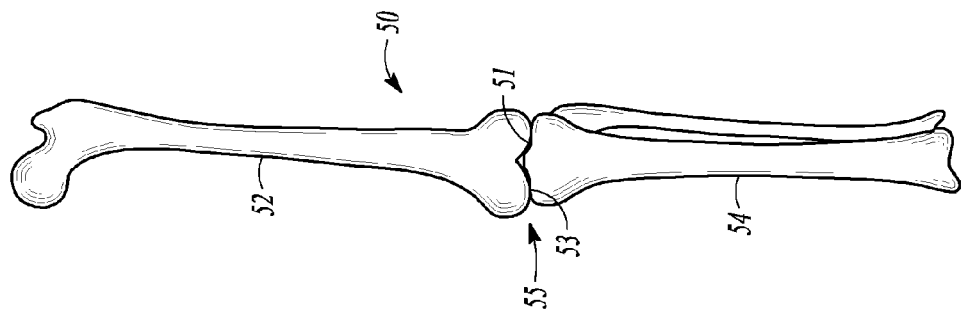

FIGS. 4, 5, and 6 are front elevation views illustrating a knee joint 50 with normal or neutral pre-surgical limb alignment, varus pre-surgical limb alignment, and valgus pre-surgical limb alignment, respectively. The knee joint 50 can be formed by portions of a distal end 51 of a femur 52 and a proximal end 53 of a tibia 54. Assuming that the surgeon's goal is to maintain or achieve "neutral" limb alignment in each of these three examples, with reference to the "neutral" example in FIG. 4 the surgeon would select a tibial cut depth and tibial implant on the medial side 55 of the knee joint 50 that maintains the joint line 8 (FIG. 1) roughly at its current location. With reference to the "varus" example in FIG. 5, the surgeon would select a tibial cut depth and tibial implant on the medial side 55 of the knee joint 50 that raises the joint line 8 (FIG. 1) from its current location. Finally, with reference to the "valgus" example in FIG. 6, the surgeon would select a tibial cut depth and tibial implant on the medial side 55 of the knee joint 50 that lowers the joint line 8 (FIG. 1) from its current location. Correction of the knee joint 50 would also involve, at a minimum, one or more femoral cuts. In an example, the lateral side of the knee joint 50 can alternatively be cut for correction of the knee joint 50. Establishing a neutral limb alignment may not always be desirable. For example, a surgeon may decide that with a particular patient establishing a mechanical axis that results in a slightly varus or a slightly valgus knee is preferable.

Figure 7:
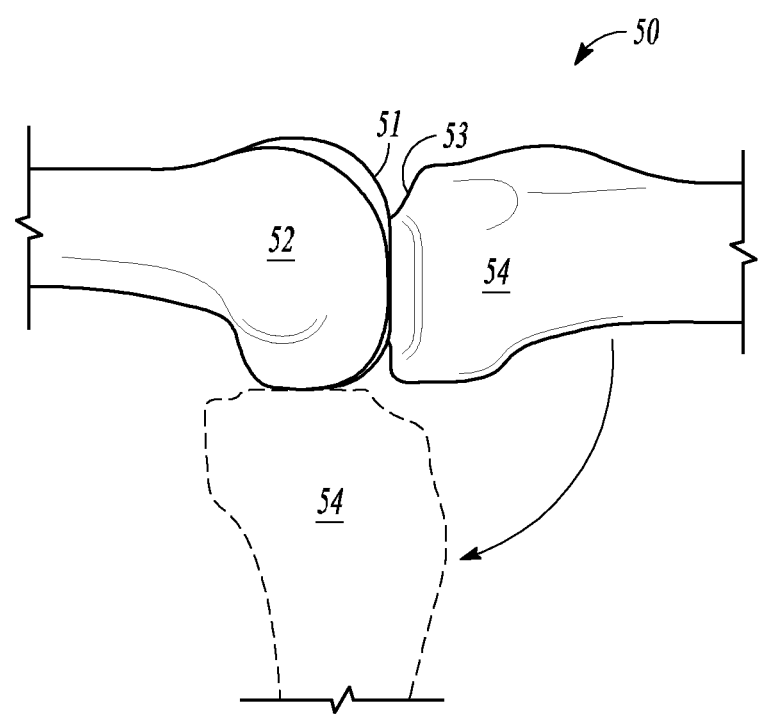
FIG. 7 is a diagram illustrating a knee joint prior to beginning a unicondylar knee replacement procedure.

FIG. 7 is a diagram illustrating the knee joint 50 prior to beginning the unicondylar knee replacement procedure. The knee joint 50 is movable from a position of "extension" as depicted by the solid line tibia 54 to a position of "flexion" as indicated by the broken line tibia 54. For purposes of clarity and simplicity of illustration, the distal end 51 of the femur 52 and the proximal end 53 of the tibia 54 are not depicted with the type of damage that would typically be found in a patient in need of a knee replacement (full or partial). However, one or both of the distal end 51 of the femur 52 and the proximal end 53 of the tibia 54 would contain damaged bone and/or tissue, thus necessitating surgery.

One goal of unicondylar knee surgery can be to resect portions of the distal end 51 of the femur 52 and the proximal end 53 of the tibia 54 and replace those portions with femoral and tibial knee replacement components. These femoral and tibial knee replacement components function to, among other things, restore operation of the patent's knee joint and relieve pain. In an example, the femoral and tibial resections can be performed using a saw blade and a corresponding guide, with the knee joint 50 in flexion or extension. The resection procedure can involve preoperative planning steps that are performed prior to the surgery, using images of the patient's knee, in order to determine the desired locations for the various cuts. The subject matter of the present patent application provides a system and method for performing such pre-operative planning.

Figure 8:
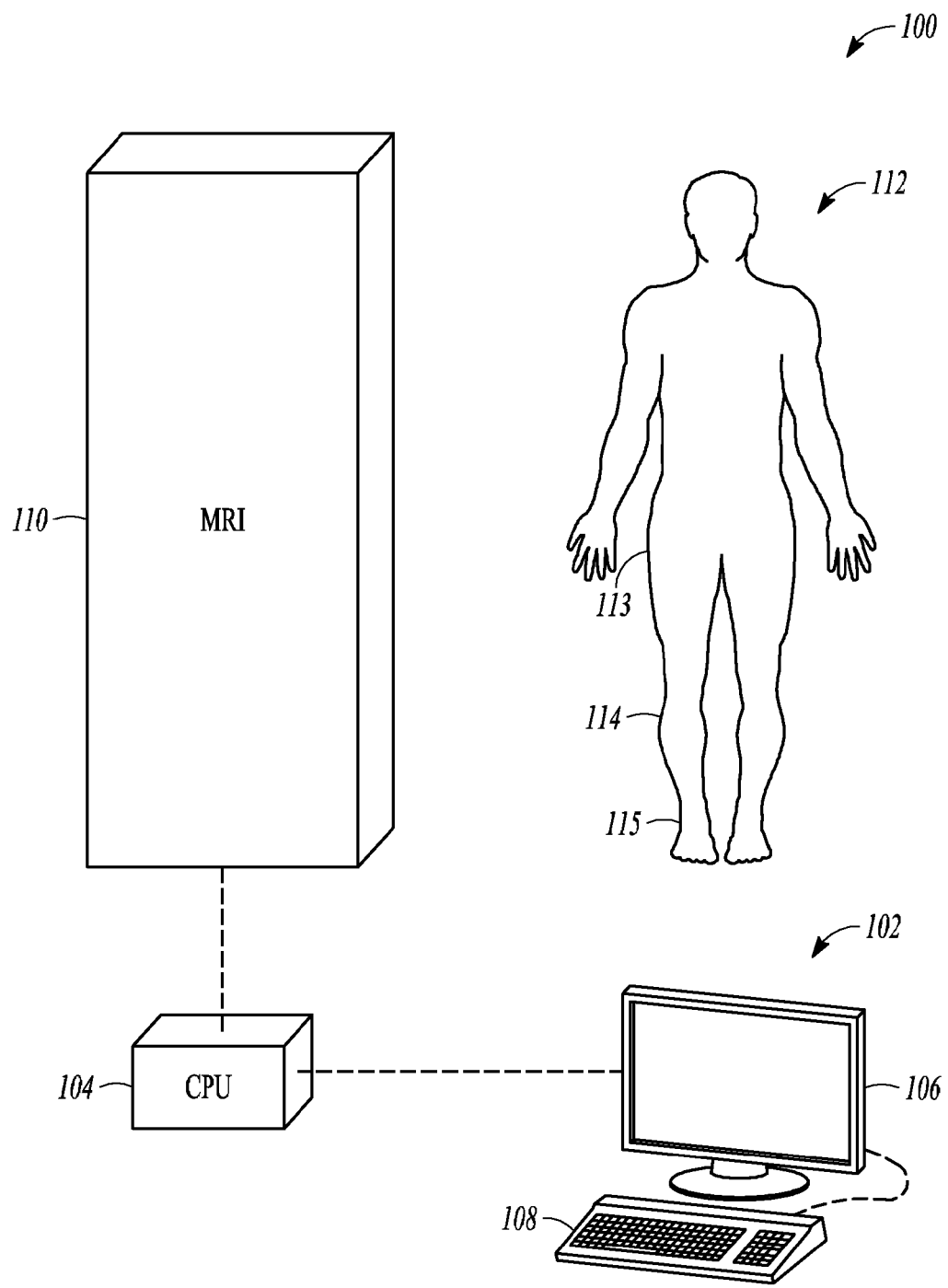
FIG. 8 is an example of a pre-operative planning system in accordance with the present application.

FIG. 8 is an example of a pre-operative planning system 100 in accordance with the present application, which can generally include a computer 102 having a CPU 104, a monitor or screen 106, and operator interface controls 108. The CPU 104 can include a processor circuit that can include or be coupled to a device-readable medium including instructions that, when performed by the processor circuit, can cause the circuit to perform the method acts described herein. The computer 102 can, for example, be linked to a medical imaging machine 110, such as a magnetic resonance imaging ("MRI") machine. In operation, a patient 112 can be positioned in the imaging machine 110 in order to obtain images of a hip joint 113, a knee joint 114, and/or an ankle joint 115, wherein the knee joint 114 is to be the subject of an arthroplasty procedure. As discussed in greater detail below, in an example, the patient 112 can have the hip joint 113, the knee joint 114, and the ankle joint 115 scanned in the imaging machine 110. The imaging machine 110 can, for example, be operable to make a plurality of scans of the hip, knee, and ankle joints 113, 114, and 115, wherein each scan pertains to a thin slice of a single joint or multiple joints.

While the examples below will be discussed in the context of the imaging being via MRI, any suitable imaging technique can be used by which a volumetric, three-dimensional image data set of the patient's joint can be obtained. In an example, computed tomography ("CT") or X-ray imaging can alternatively be employed.

Figure 10:
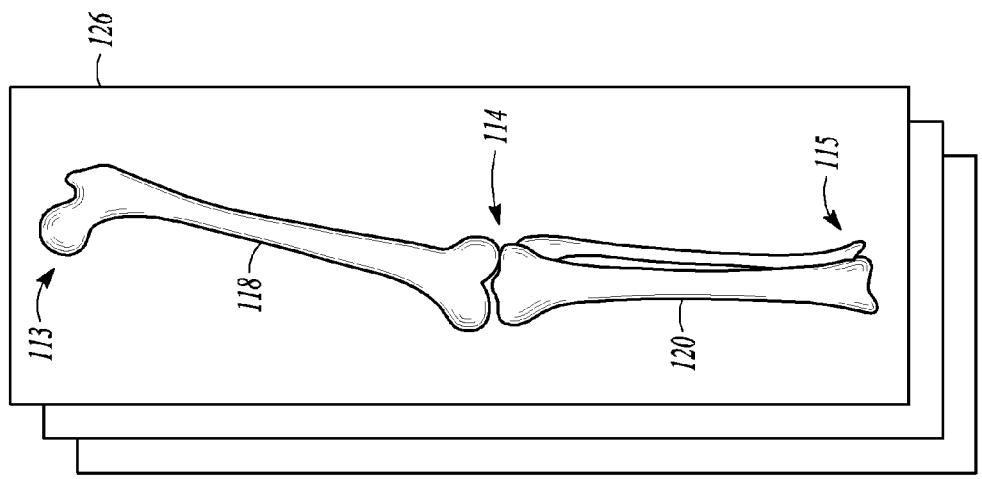
FIGS. 9 and 10 are diagrams illustrating two-dimensional scanning of a patient's leg.
Figure 9:
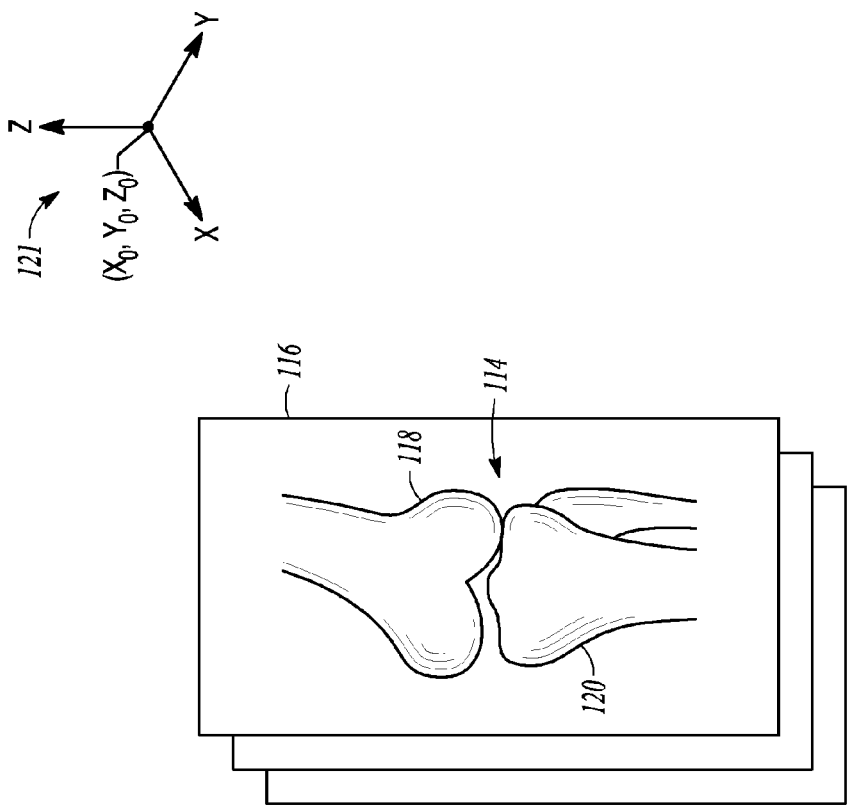

Turning next to FIGS. 9 and 10, in an example, the patient's leg bone structure can undergo two types of scanning in the imaging machine 110. With reference to the first type of scanning, the patient's knee 114, including portions of the femur 118 and the tibia 120, can be scanned in an MRI knee coil to generate a plurality of two-dimensional ("2D") knee coil MRI images 116 of the patient's knee 114 as illustrated in FIG. 9. In an example, the knee coil 2D images 116 include a plurality of coronal images, a plurality of axial images, and a plurality of sagittal images. In other examples, the knee coil 2D images 116 can be any combination of coronal, sagittal, and/or axial views. The knee coil 2D images 116 can have a location and orientation in a global coordinate system 121 having an origin $(X_0, Y_0, Z_0)$. Any suitable MRI imaging spacing can be utilized for the 2D knee coil images 116.

With reference to the second type of scanning illustrated in FIG. 10, the patient's entire leg length, or portions thereof that include the patient's hip 113, knee 114, and ankle 115, can be scanned in the MRI body coil to generate a plurality of 2D body coil MRI images 126 of the patient's entire leg length or, at least, a plurality of body coil 2D MRI images 126 at each of the patient's hip 113, knee 114, and ankle 115. In other words, the body coil 2D images 126 can either include all of hip 113, knee 114, and ankle 115, or certain portions thereof. In an example, the body coil 2D images 126 can include a plurality of coronal images, a plurality of axial images, and a plurality of sagittal images at each of the hip 113, knee 114, and ankle 115. In other examples, the body coil 2D images 126 can be any combination of coronal, sagittal, and/or axial views. The body coil 2D images 126 can have a location and orientation in the global coordinate system 121 having the origin $(X_0, Y_0, Z_0)$. Any suitable MRI imaging spacing can be utilized for the 2D body coil images 126. Upon collecting the sets of 2D images 116, 126 described above with reference to FIGS. 9 and 10, the images can be sent to the computer 102 for analysis and modeling.

Figure 11:
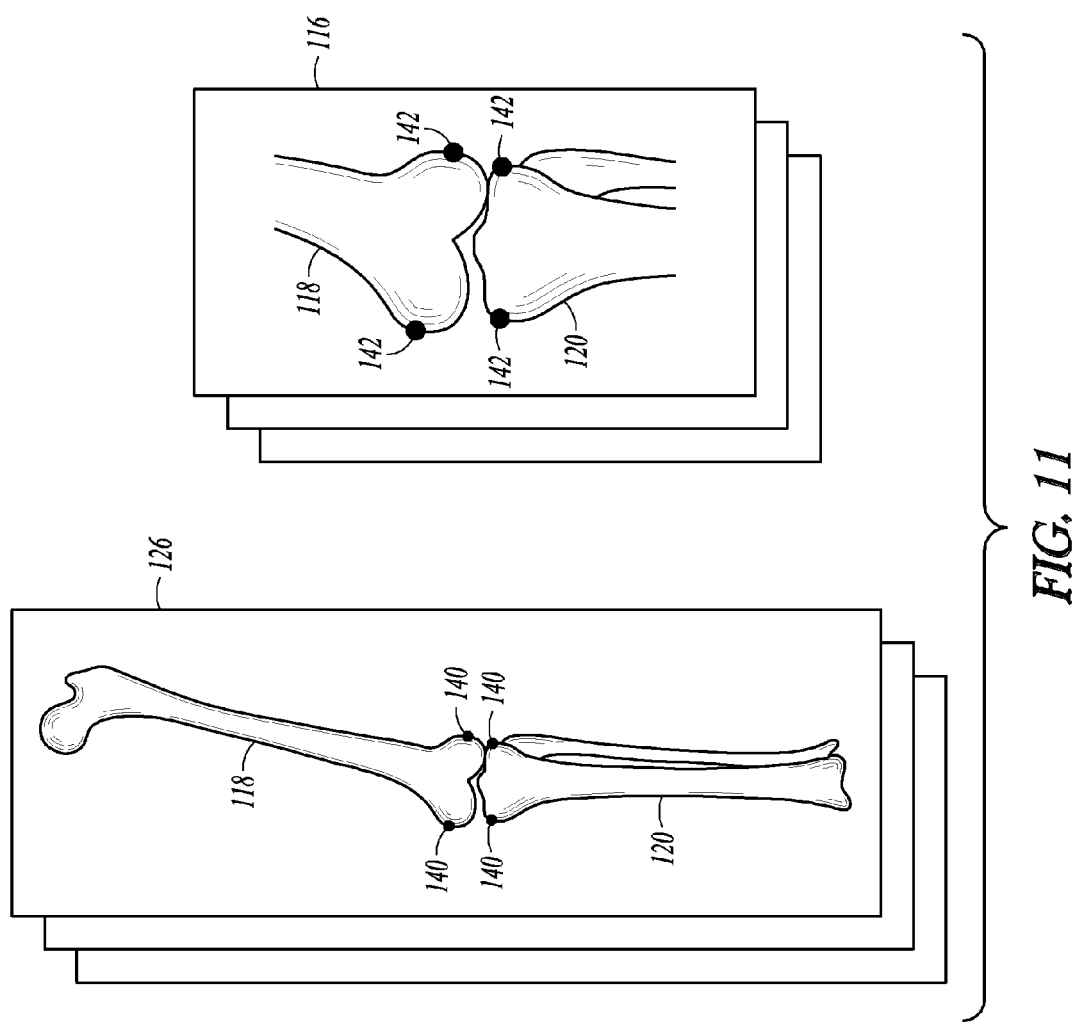
FIG. 11 is a diagram illustrating various anatomical reference points in two-dimensional knee coil images and two-dimensional body coil images.

Turning next to FIG. 11, reference points 142 can be identified on certain landmarks in the 2D knee coil images 116. Examples of such landmarks on the knee region of the femur 118 can include the center of the femoral condyle region near the trochlear groove, the most medial and lateral points of the epicondyles, or other identifiable landmarks. Examples of such landmarks on the knee region of the tibia 120 can include the medial and lateral edges of the tibial condyles, the medial and lateral transitions from the tibial plateau to the tibial shaft, or other identifiable landmarks. In an example, in order to visually identify the landmarks, an operator sitting in front of the monitor 106 can "tab" through the various coronal 2D knee coil images 116 to determine the specific coronal 2D knee coil image 116 in which the femur 118 is depicted with the largest and most clear condyle contour. When the operator visually identifies such an image, the operator can electronically "mark" a first subset of the reference points 142 on the femur 118 causing the location of the centers to be electronically stored relative to the global coordinate system 121. The operator can then "tab" through the various coronal 2D knee coil images 116 to determine the specific coronal 2D knee coil image 116 in which the tibia 120 is depicted with the largest and most clear condyle contour. When the operator visually identifies such an image, the operator can electronically "mark" a second subset of the reference points 142 on the tibia 120 causing the location of the centers to be electronically stored relative to the global coordinate system 121.

As further indicated in FIG. 11, reference points 140 can be identified on corresponding landmarks in the 2D body coil images 126. In an example, in order to visually identify the landmarks, the operator can "tab" through the various coronal 2D body coil images 126 to determine the specific coronal 2D body coil image 126 in which the femur 118 is depicted with the largest and most clear condyle contour. When the operator visually identifies such an image, the operator can electronically "mark" a first subset of the reference points 140 on the femur 118 causing the location of the centers to be electronically stored relative to the global coordinate system 121. The operator can then "tab" through the various coronal 2D body coil images 126 to determine the specific coronal 2D body coil image 126 in which the tibia 120 is depicted with the largest and most clear condyle contour. When the operator visually identifies such an image, the operator can electronically "mark" a second subset of the reference points 140 on the tibia 120 causing the location of the centers to be electronically stored relative to the global coordinate system 121.

The identification of two reference points 140/142 on the femur 118 and two reference points 140/142 on the tibia 120 is described for purposes of example and not limitation. In other examples, more than two reference points can be identified and recorded. Regardless of how many reference points 140, 142 are selected and in which type of image views the selections are made, the coordinate locations of the reference points 140, 142 can be stored for use with a transformation process as described below.

Figure 12:
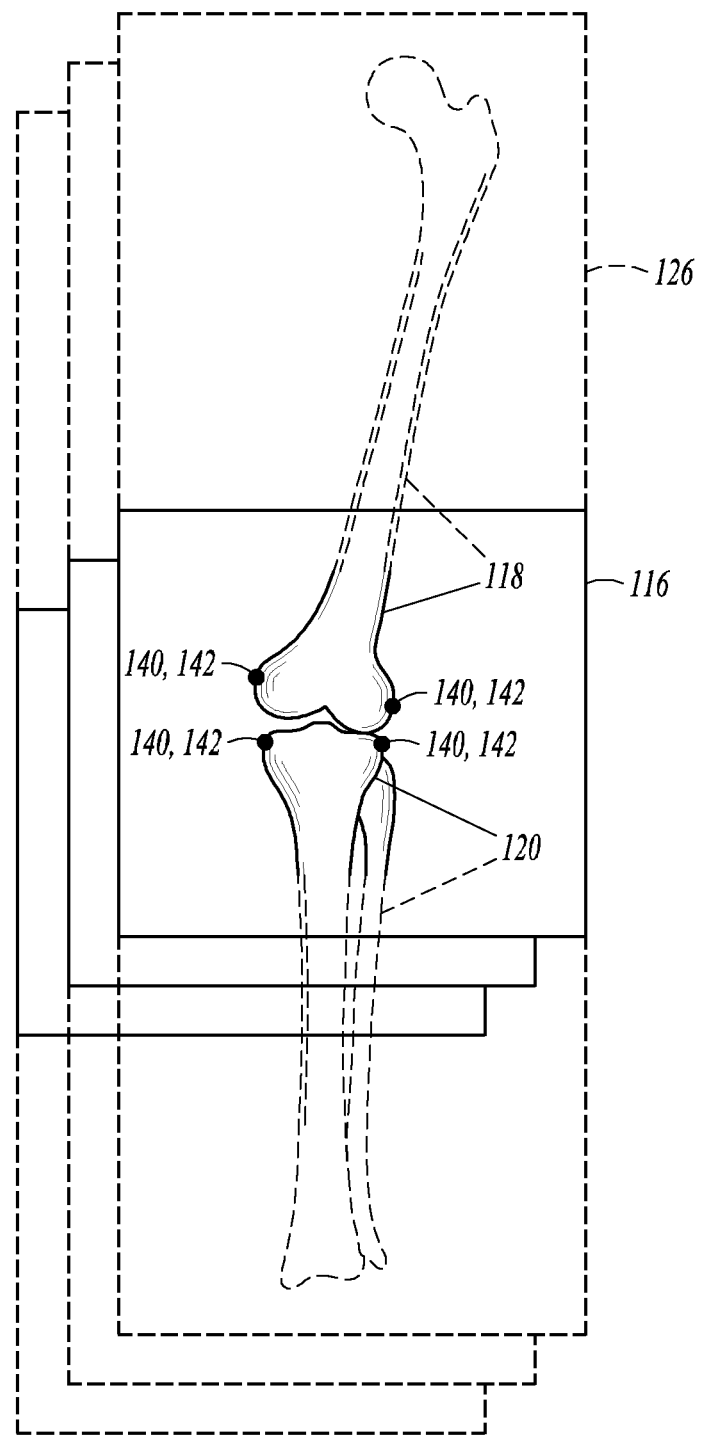
FIG. 12 is a diagrammatic depiction of a transformation process in which two-dimensional knee coil images are matched to two-dimensional body coil images in a global coordinate system.

FIG. 12 is a diagrammatic depiction of a "transformation" process in which the 2D knee coil images 116 can be moved to the location of the 2D body coil images 126 in the global coordinate system 121, or vice versa. Specifically, a transformation can be run for the reference points 140, 142 to cause the 2D knee coil images 116 to generally positionally match the 2D body coil images 126 with respect to both location and orientation. The exemplary transformation process can cause the coronal, axial, and sagittal 2D knee coil images 116 to move to and positionally match the coronal, axial, and sagittal 2D body coil images 126 in the global coordinate system 121.

Any suitable transformation process can be used to achieve the image transformation. In an example, the transformation occurs by bringing the points 142 of the 2D knee coil images 116 as close as possible to the points 140 of the 2D body coil images 124. The closeness of the two sets of points can be evaluated, such as by determining the sum of squared distances from points in the first set to the second set, and applying manipulations of rotation and translation to the points and associated images for the distal femur and proximal tibia.

In another example, the 2D knee coil images 116 can be segmented and converted into a 3D bone model. Reference points 140 can be identified in the 2D body coil images 126 and positionally matched to corresponding landmark points 142 in the 3D bone model using a suitable algorithm, such as an iterative closest point algorithm. In another example, the 2D knee coil images 116 can be segmented and converted into a 3D bone model and splines can be defined along the bone contours in the 2D body coil images 126, thereby enabling a "contour to contour" positional matching process to be performed. In another example, image intensity variations in the 2D knee coil images 116 can be identified and positionally matched to corresponding image intensity variations identified in the 2D body coil images 126. Numerous other positional matching and transformation processes are also contemplated. Further, the positional matching and transformation processes can be manual, automated, or a combination of the two.

Figure 13:
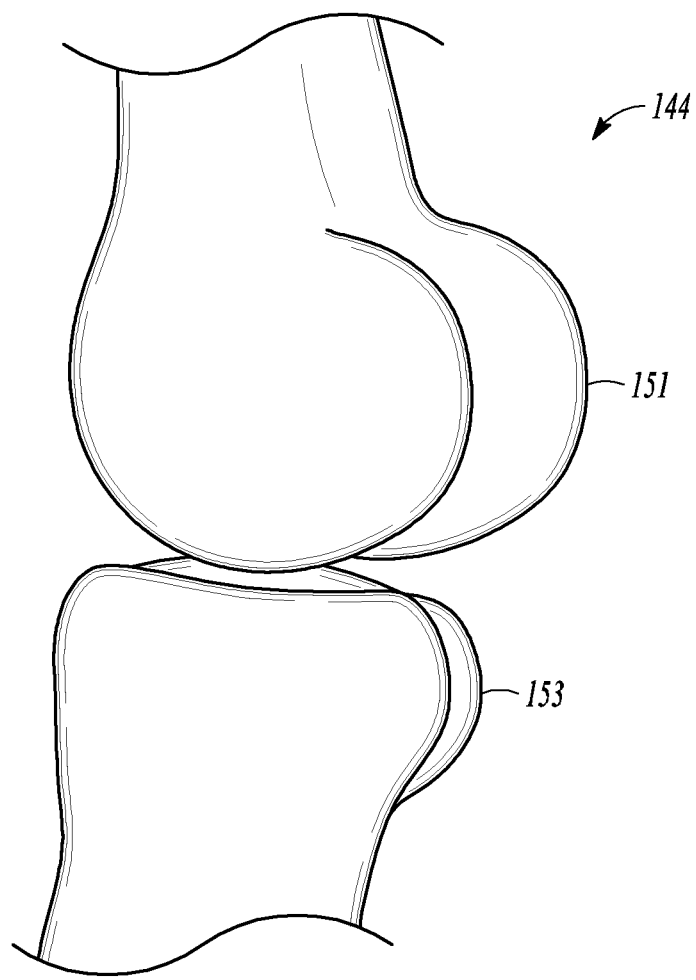
FIG. 13 is diagram illustrating a three-dimensional image of a leg.

Regardless of the type of transformation process that is used, the output of the transformation process can be, for example, a data file containing data corresponding to a plurality of (X,Y,Z) coordinates that together define a 3D image of the tibia and femur. In an example, the data can be stored as a stereolithography ("STL") file, although any suitable file type can be used. The data file can subsequently be processed by the CPU 104 of the computer 102, and a 3D image 144 of the leg can be displayed on the monitor 106, as depicted in FIG. 13. The 3D image 144 can include a 3D femur 151 and a 3D tibia 153. This 3D image 144 can be used to perform a wide range or pre-operative planning steps, as described in further detail below.

The imaging steps set forth above were described as being performed with the patient's knee joint 114 in extension. Optionally, the patient's knee joint 114 can also be placed in flexion (full or partial) prior to obtaining the imaging data. For example, in many patients who have arthritis or another condition that affects the knee joint, it can be helpful for the surgeon to assess the joint space between the distal end of the femur 118 and the proximal end of the tibia 120 in flexion to properly size the orthopedic prosthesis that will eventually be implanted within the knee joint 114 to optimally reconstruct the joint. In an example, a suitable brace can be applied about the knee joint 114 in order to place the joint in flexion when the patient's leg is extended. In this manner, when the imaging data is obtained, the femur 118, the tibia 120, and the surrounding soft tissue can all be viewed to allow the surgeon to evaluate soft tissue laxity, which can assist the surgeon to properly determine the size and position of the orthopedic prosthesis.

As discussed above, the 3D image 144 of the leg can be used by a surgeon to perform numerous pre-operative planning tasks prior to making any incisions in the patient. In an example, the pre-operative planning tasks can assist the surgeon in making determinations regarding joint alignment, implant size, and resection locations.

In an example, a pre-operative planning method can begin by allowing selection of one or more femoral and/or tibial anatomical reference points on the 3D image 144 and/or the 2D images 116, 126 by an operator, such as a surgeon. Particularly, the 3D image 144 presented on the monitor 106 can be manipulated, such as by rotating the 3D image 144 or adjusting the size of the displayed 3D image 144. The pre-operative planning system 100 can also provide the capability of isolating the 3D femur 151 from the 3D tibia 153 (or vice versa) such that only one of the bones is displayed on the monitor 106. In addition to allowing isolation of the 3D femur 151 or the 3D tibia 153, the pre-operative planning system 100 can provide the capability of isolating selected portions of the 3D femur 151 or the 3D tibia 153. In an example, the surgeon can isolate the 3D femur 151 from the 3D tibia 153, and further isolate a proximal end or a distal end of the 3D femur 151 from the remaining portions of the femur to simplify the displayed image when the focus is only on a certain portion of the bone. The various scan plane views of the 2D knee coil images 116 or the 2D body coil images 126 can be presented to the surgeon in addition to the 3D image 144 or instead of the 3D image 144. In an example, the 2D images 116, 126 can also be manipulated, such as by adjusting the size of the displayed 2D images 116, 126 (e.g., "zooming in" or "zooming out").

The femoral and/or tibial anatomical reference points can be "selected" using, for example, the operator interface controls 108 described above. The selected femoral and/or tibial anatomical reference points can thereafter be stored for later use, such as in a memory component of the computer system 102. In various examples, the selection of the femoral anatomical reference points can be performed automatically by the computer system 102, or through a combination of automated and manual steps.

As will be described with reference to FIGS. 14A-14D, in an example, the one or more femoral anatomical reference points can include a femoral head center, a middle notch point, an anterior trochlea point, a medial epicondylar point, and a lateral epicondylar point. However, the foregoing reference points are described for purposes of example and not limitation. Thus, additional and/or different reference points can be selected in other examples.

The femoral anatomical reference points can be used for several pre-operative planning purposes, such as defining or generating anatomical axes and anatomical planes which can be used to determine a desired joint alignment.

Figure 14A:
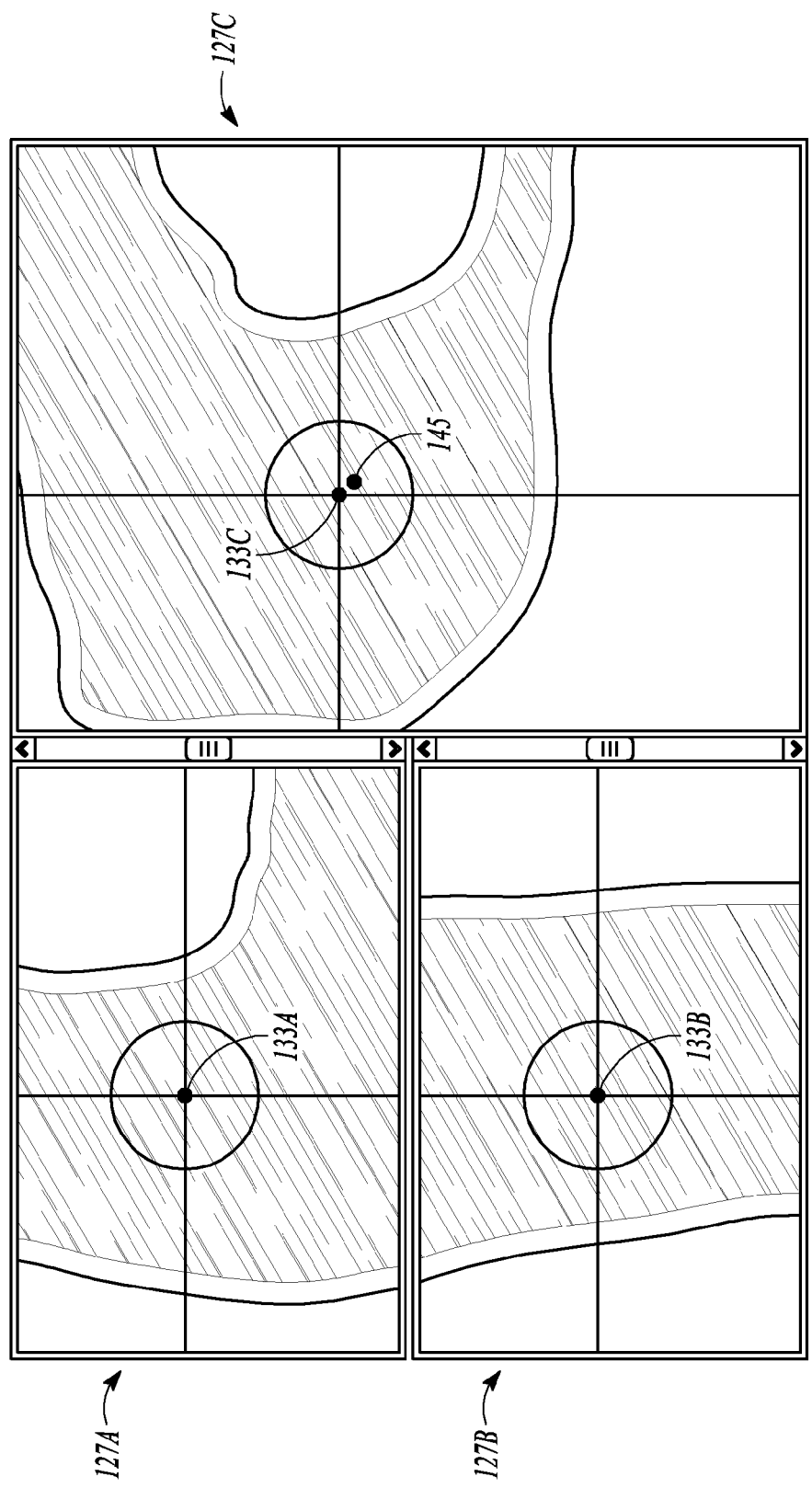
FIGS. 14A-14E are diagrams illustrating exemplary images that can be presented for selecting anatomical reference points associated with a femur.

FIG. 14A is a diagram illustrating three exemplary views that can be presented to the surgeon for selection of a femoral head point 145. As shown in FIG. 14A, in an example, the pre-operative planning system 100 can be designed to show a coronal view 127A of a proximal head of the 2D femur 118, a sagittal view 127B of the proximal head of the 2D femur 118, and an axial view 127C of the proximal head of the 2D femur 118. Upon analyzing the various views, the surgeon can electronically mark a desired femoral head point 133A in the coronal view 127A, a desired femoral head point 133B in the sagittal view 127B, and a desired femoral head point 133C in the axial view 127C. In an example, the CPU 104 of the computer 102 can then be configured to process the locations of the femoral head points 133A-133C and derive a femoral head point 145 that represents a closest fit between the femoral head points 133A-133C. The femoral head point 145 can be derived in any suitable manner, such as by selection of the center of the femoral head in any two views, which can fully constrain its position in three dimensions. The location of the femoral head point 145 can be electronically stored relative to the global coordinate system 121.

Figure 14B:
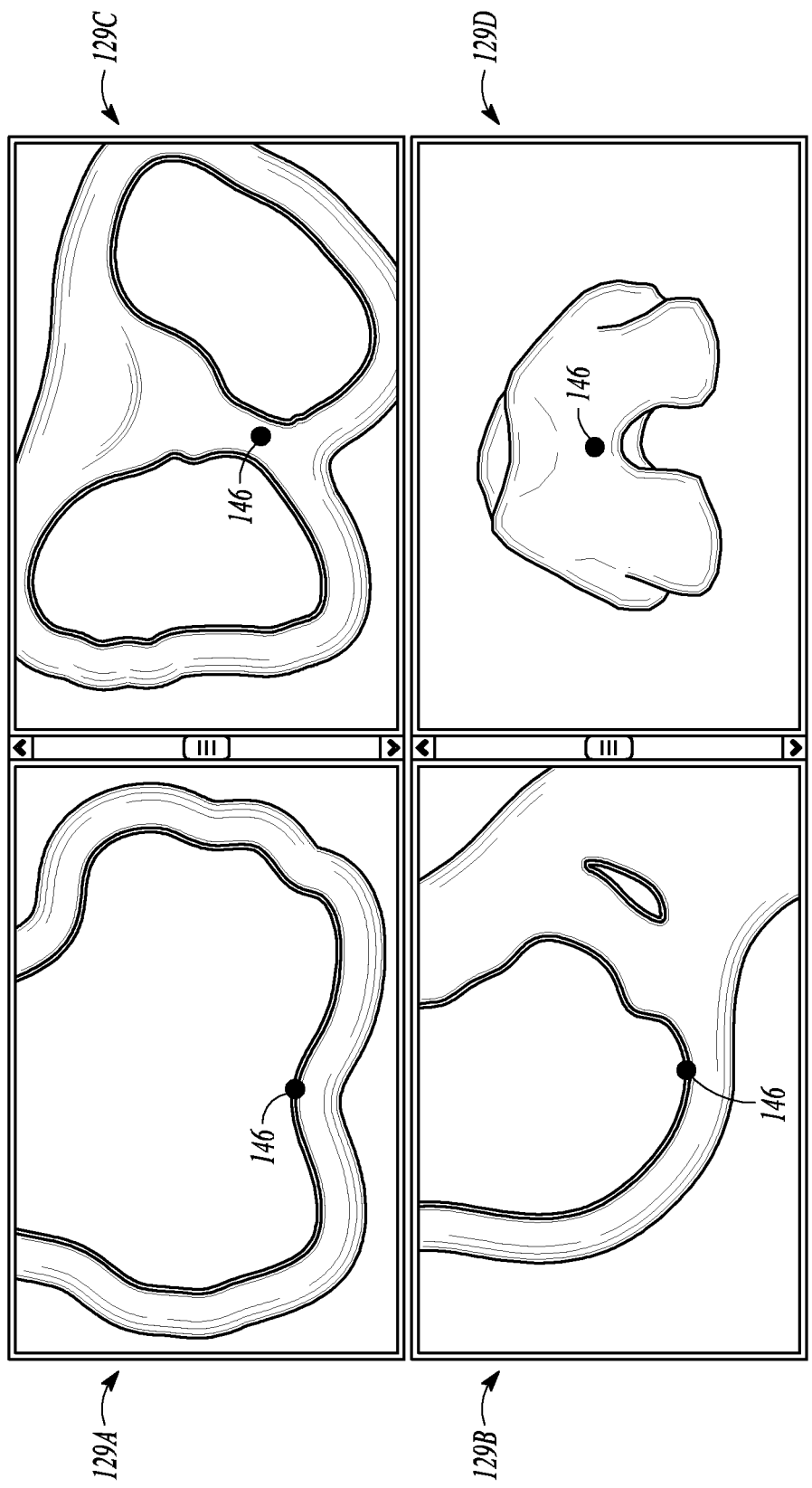

FIG. 14B is a diagram illustrating four exemplary views that can be presented to the surgeon for selection of a middle notch point 146. As shown in FIG. 14B, in an example, the pre-operative planning system 100 can be designed to show a coronal view 129A of a distal end of the 2D femur 118, a sagittal view 129B of the distal end of the 2D femur 118, an axial view 129C of the distal end of the 2D femur 118, and a 3D view 129D of the distal end of the 3D femur 151. In an example, the surgeon can manipulate the 3D view 129D on the monitor 106 until a desired orientation has been obtained. The surgeon can further "tab" through the various 2D knee coil images 116 and/or the 2D body coil images 126 to find the views 129A-129C with the largest and most clear condyle contour. The surgeon can then use the various views 129A-129D to identify and electronically "mark" the middle notch point 146 causing the location of the middle notch point to be electronically stored relative to the global coordinate system 121. The views 129A-129D can be "linked" such that marking the middle notch point 146 in one of the views causes the point to be displayed in each of the other views. Thus, the surgeon can mark the middle notch point 146 in any one of the views 129A-129D and confirm the proper location of the point in the other of the views 129A-129D.

In other examples, the surgeon can electronically mark a middle notch point in each of the views, and the CPU 104 of the computer 102 can then be configured to process the marked locations and derive a middle notch point 146 that represents a closest fit between the marked points from the various views 129A-129D as discussed above with reference to the femoral head point 145 of FIG. 14A.

Figure 14C:
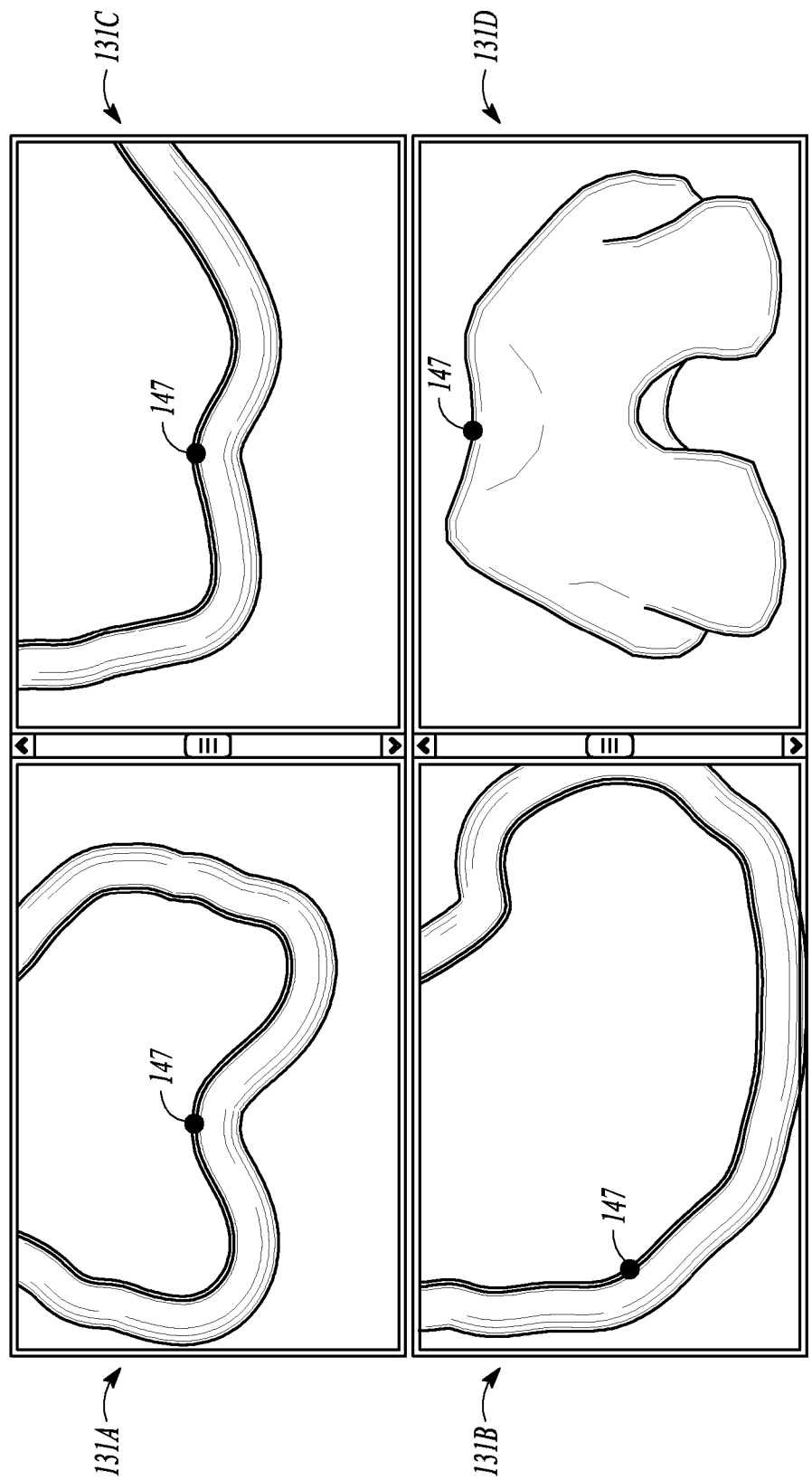

FIG. 14C is a diagram illustrating four exemplary views that can be presented to the surgeon for selection of an anterior trochlea point 147, including a coronal view 131A of a distal end of the 2D femur 118, a sagittal view 131B of the distal end of the 2D femur 118, an axial view 131C of the distal end of the 2D femur 118, and a 3D view 131D of the distal end of the 3D femur 151.

Figure 14D:
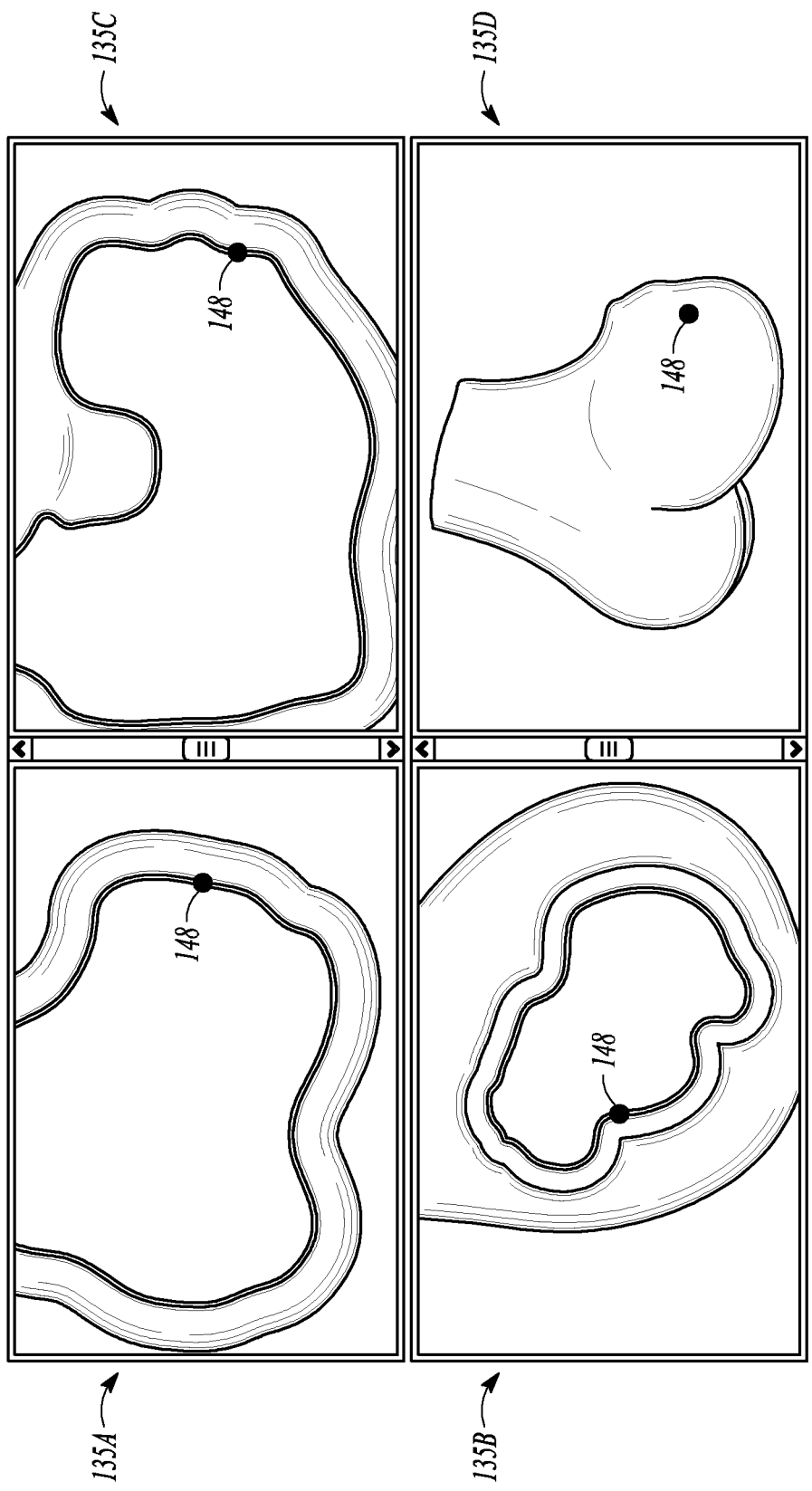

FIG. 14D is a diagram illustrating four exemplary views that can be presented to the surgeon for selection of a medial epicondylar point 148, including a coronal view 135A of a distal end of the 2D femur 118, a sagittal view 135B of the distal end of the 2D femur 118, an axial view 135C of the distal end of the 2D femur 118, and a 3D view 135D of the distal end of the 3D femur 151.

Figure 14E:
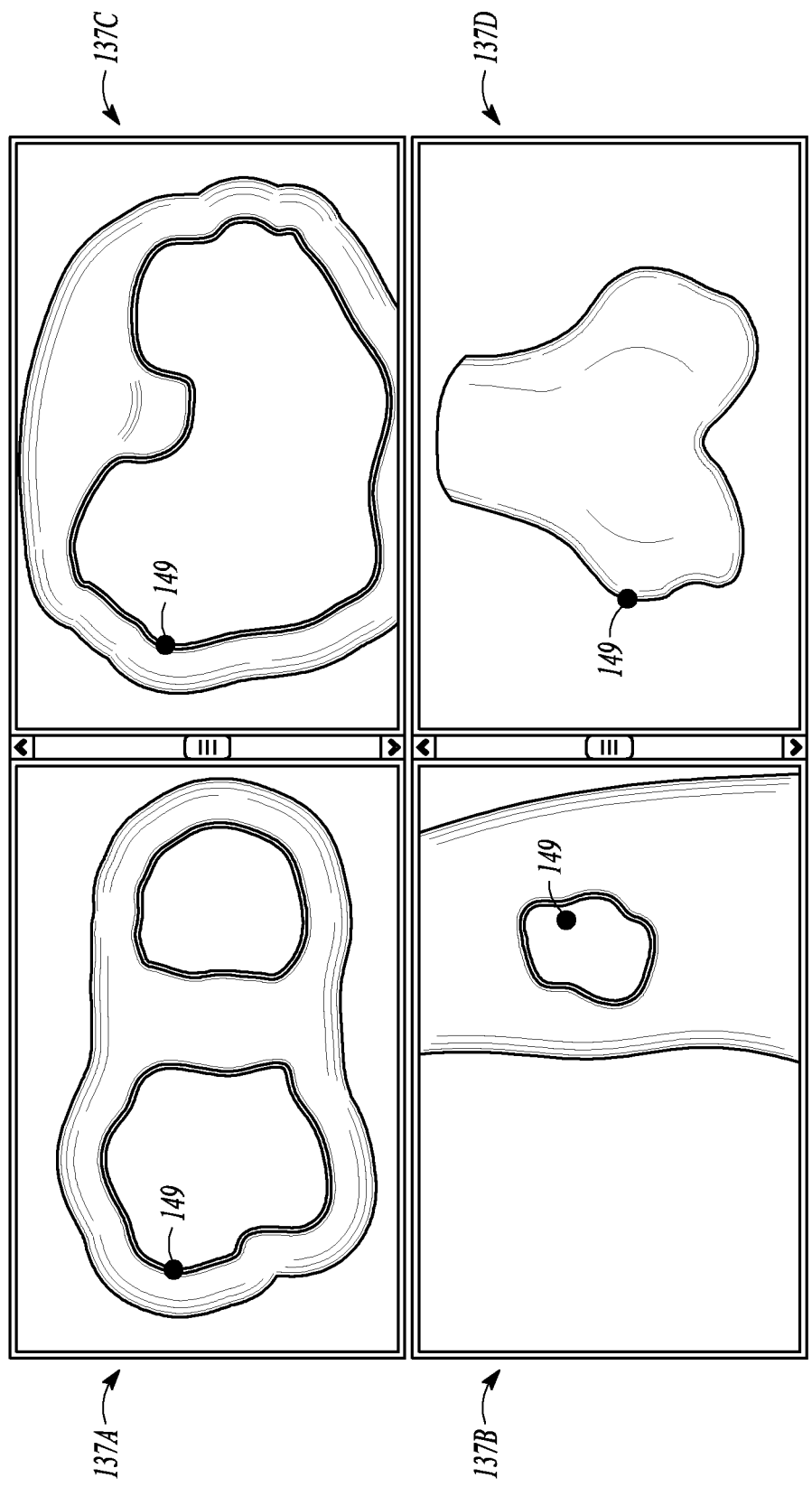

FIG. 14E is a diagram illustrating four exemplary views that can be presented to the surgeon for selection of a lateral epicondylar point 149, including a coronal view 137A of a distal end of the 2D femur 118, a sagittal view 137B of the distal end of the 2D femur 118, an axial view 137C of the distal end of the 2D femur 118, and a 3D view 137D of the distal end of the 3D femur 151.

With reference to FIGS. 14C-14E, the surgeon can determine and electronically mark the anterior trochlea point 147, medial epicondylar point 148, and lateral epicondylar point 149 in a manner similar to that described above for determining and electronically marking either the femoral head point 145 (FIG. 14A) or the middle notch point 146 (FIG. 14B).

Once the desired femoral anatomical reference points are selected and marked in any suitable manner such as those described above, the pre-operative planning process can continue by, for example, deriving one or more femoral anatomical reference axes using the anatomical reference points. Examples of such femoral anatomical reference axes are described below with reference to FIGS. 15A-15D.

FIG. 15A is a frontal view of the 3D femur 151 illustrating a derived femoral mechanical axis 152 extending between a proximal end 154 and a distal end 156 of the 3D femur 151. In an example, the derived femoral mechanical axis 152 extends through the femoral head point 145 (FIG. 14A) at the proximal end 154 of the 3D femur 151 and the middle notch point 146 (FIG. 14B) at the distal end 156 of the 3D femur 151. For purposes of reference, the femoral anatomical axis 158 of the 3D femur 151 is also depicted in FIG. 15A. Although varying from patient to patient, average differences between the femoral mechanical axis 152 and the femoral anatomical axis 158 can be about 6-7 degrees in varus or valgus angle, and about 2-3 degrees in flexion angle.

FIG. 15B is a distal end view of the 3D femur 151 illustrating a derived epicondylar axis 160 at the distal end 156. In an example, the derived epicondylar axis 160 extends through the medial epicondylar point 148 (FIG. 14D) on a medial side 161 of the femur 151 and through the lateral epicondylar point 149 (FIG. 14E) on a lateral side 162 of the femur 151.

FIG. 15C is another distal end view of the 3D femur 151 illustrating a derived anterior-posterior ("AP") axis 164 at the distal end 156. In an example, the derived AP axis 164 extends through the middle notch point 146 (FIG. 14B) located about midway between an anterior side 166 and a posterior side 167 of the femur 151 and is projected toward a mid-point of the anterior trochlea.

Figure 16:
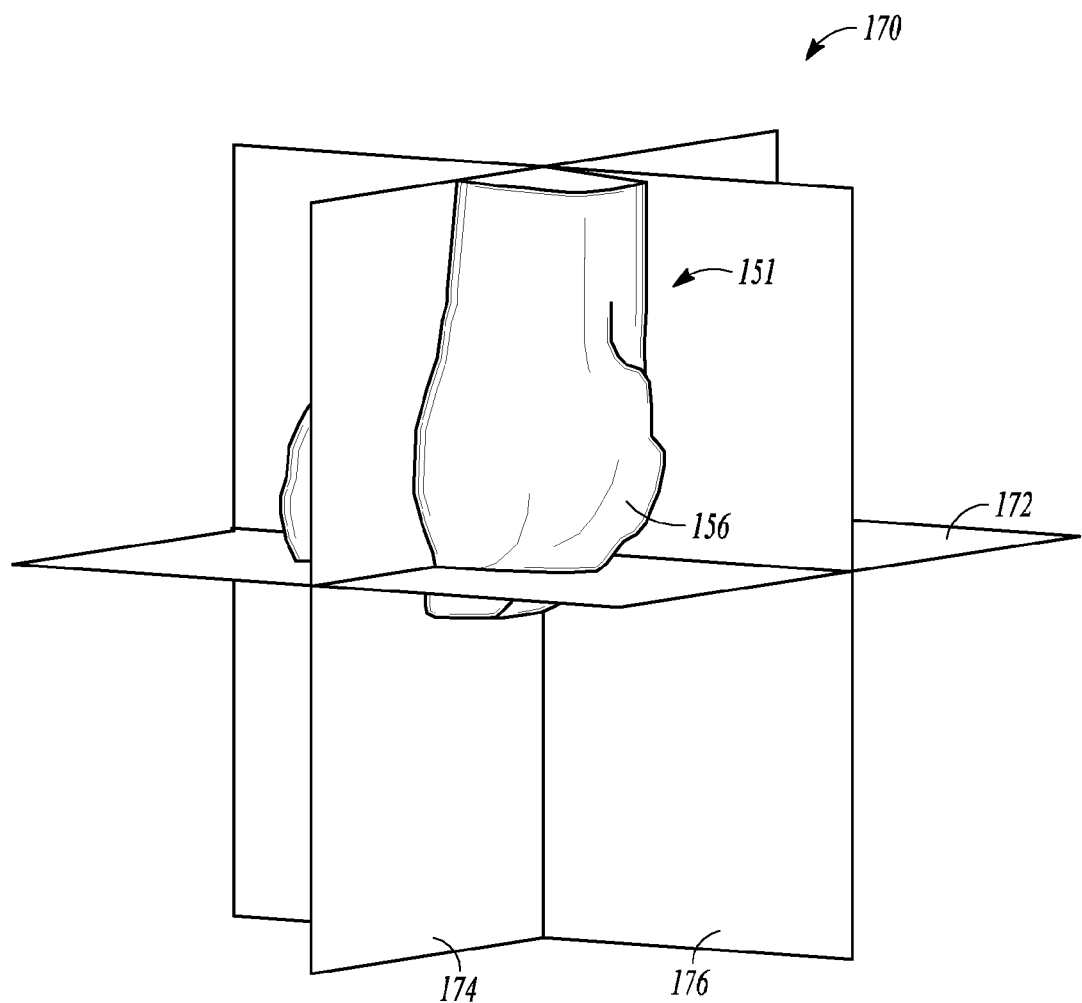
FIG. 16 is a perspective view of a distal end of the three-dimensional femur illustrating derived femoral anatomical reference planes in a medical coordinate system.

FIG. 16 is a perspective view of the distal end 156 of the 3D femur 151 illustrating derived anatomical reference planes in a medical coordinate system 170. Particularly, as shown in FIG. 16, the medical coordinate system 170 can include a femoral axial plane 172, a femoral coronal plane 174, and a femoral sagittal plane 176. In various examples, the femoral axial plane 172 can be defined by a plane that extends through the middle notch point 146 perpendicular to the derived femoral mechanical axis 152, the femoral coronal plane 174 can be defined by a plane that extends through the middle notch point 146 and parallel to the derived epicondylar axis 160, and the femoral sagittal plane 176 can be defined by a plane that extends through the middle notch point 146 and is perpendicular to the femoral axial plane 172 and the femoral coronal plane 174. A medical coordinate system 170 that includes additional and/or different planes is also contemplated.

Figure 17B:
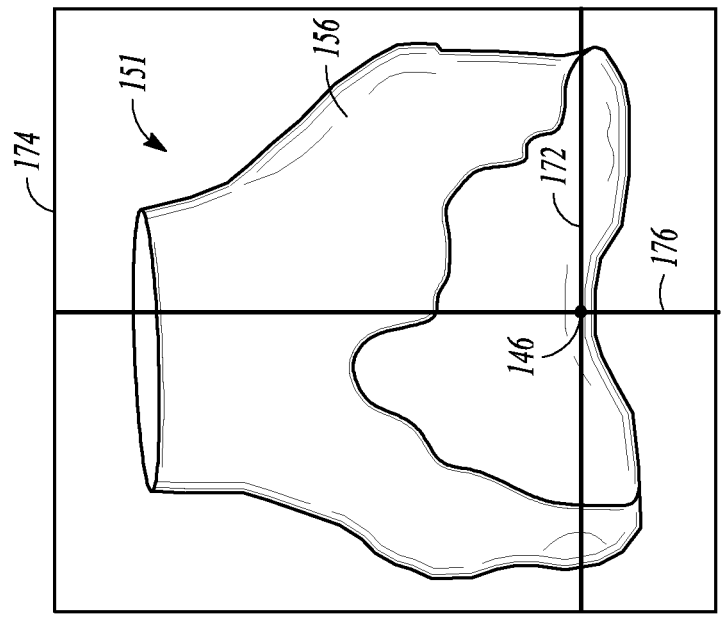
FIGS. 17A and 17B are sagittal plane and coronal plane views, respectively, illustrating the derived femoral anatomical reference planes.
Figure 17A:
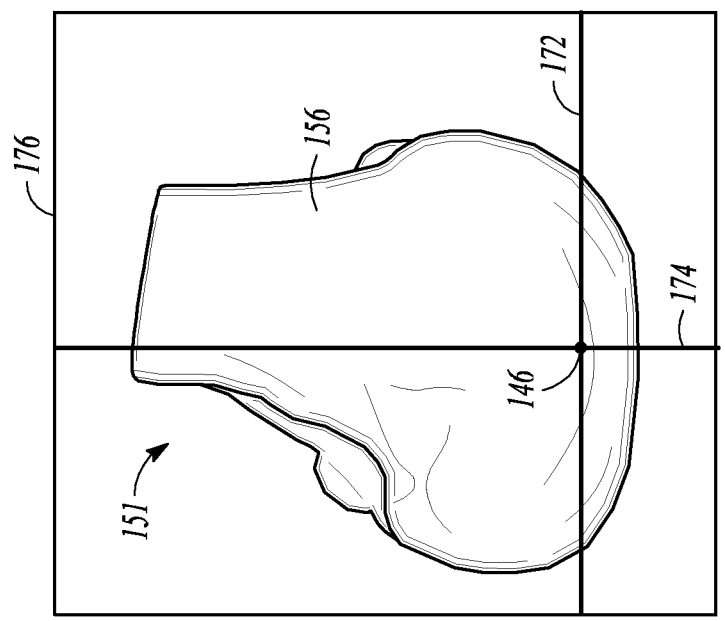

FIG. 17A is a sagittal plane view 176 of the distal end 156 of the 3D femur 151 illustrating the femoral axial plane 172 and the femoral coronal plane 174 extending through the middle notch point 146. FIG. 17B is a coronal plane view 174 of the distal end 156 of the 3D femur 151 illustrating the femoral axial plane 172 and the femoral sagittal plane 176 extending through the middle notch point 146.

With further reference to FIGS. 16 and 17A-17B, the intersection line between the femoral sagittal plane 176 and the femoral axial plane 172 of the medical coordinate system 170 can define a varus-valgus rotation axis. The intersection line between the femoral coronal plane 174 and the femoral axial plane 172 of the medical coordinate system 170 can define a flexion-extension rotation axis.

The pre-operative planning process can continue by allowing the surgeon to select one or more tibial anatomical reference points on the 3D image 144 and/or the 2D images 116, 126. Similar to the femoral anatomical reference points, the tibial anatomical reference points can be "selected" using, for example, the operator interface controls 108 described above.

As will be described with reference to FIGS. 18A and 18B, in an example, the one or more tibial anatomical points can include a medial malleoli point, a lateral malleoli point, a medial spine point, and a lateral spine point. However, the foregoing reference points are described for purposes of example and not limitation. Thus, additional and/or different reference points can be selected in other examples.

Like the femoral anatomical reference points, the tibial anatomical reference points can be used for several pre-operative planning purposes, such as defining or generating anatomical axes and anatomical planes which can be used to determine a desired joint alignment.

FIG. 18A is a diagram illustrating an exemplary view that can be presented to the surgeon for selection of a medial malleoli point 180 and a lateral malleoli point 182. As shown in FIG. 18A, the pre-operative planning system 100 can be designed to show an axial view 184 of a distal end of the 2D tibia 120. Other views, such as coronal and sagittal 2D views or a view of the 3D tibia 153, can also or alternatively be displayed. Upon analyzing the one or more views, the surgeon can electronically mark the medial malleoli point 180 and the lateral malleoli point 182 in a manner similar to that described above with reference to the femoral anatomical reference points in FIGS. 14A-14E.

FIG. 18B is a diagram illustrating exemplary views that can be presented to the surgeon for selection of a medial spine point 186 and a lateral spine point 188 on a tibial spine 189. As shown in FIG. 14B, the pre-operative planning system 100 can be designed to show, for example, an axial view 190 of a proximal end of the 2D tibia 120 and a 3D view 192 of the proximal end of the 3D tibia 153. In an example, other views such as coronal and sagittal 2D views can also or alternatively be displayed. Upon analyzing the various views, the surgeon can electronically mark the medial spine point 186 and the lateral spine point 188 in a manner similar to that described above with reference to the femoral anatomical reference points in FIGS. 14A-14E.

Once the desired tibial anatomical reference points are selected and marked, the pre-operative planning process can continue by, for example, deriving one or more tibial anatomical reference axes using the anatomical reference points. Examples of such tibial anatomical reference axes are described below with reference to FIGS. 19A and 19B.

Figure 19B:
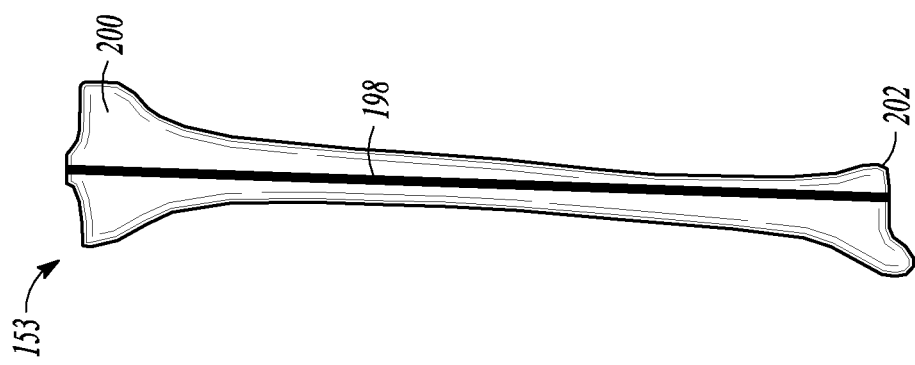
FIGS. 19A and 19B are diagrams of a three-dimensional tibia illustrating various axes derived from the tibial anatomical reference points.
Figure 19A:
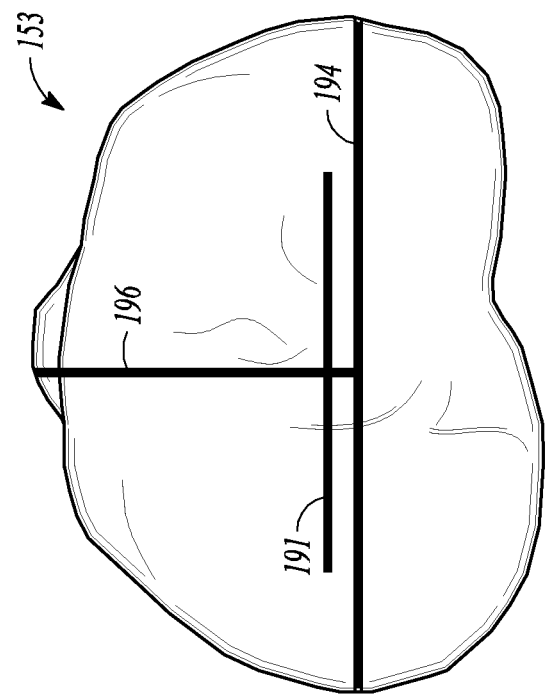

FIG. 19A is a proximal end view of the 3D femur 153 illustrating a derived tibial medial-lateral axis 194 and a derived tibial anterior-posterior axis 196. In an example, the derived medial-lateral axis 194 can be created by a line intersecting the approximate centers of the medial and lateral tibia plateaus, or alternatively perpendicular to an anterior-posterior axis derived by locating the center of the posterior cruciate ligament attachment point and the medial one-third of the tibial tuberosity. The anterior-posterior axis 196 will be substantially perpendicular to the selected medial-lateral axis 194 intersecting the medio-lateral center of the tibia that is manually selected or automatically defined by the associated software.

FIG. 19B is a frontal view of the 3D tibia 153 illustrating a derived tibial mechanical axis 198 extending between a proximal end 200 and a distal end 202 of the 3D tibia 153. In an example, the derived tibial mechanical axis 198 extends through a mid-point between the medial spine point 186 and the lateral spine point 188 (FIG. 18B) at the proximal end 200 and a mid-point between the medial malleoli point 180 and the lateral malleoli point 182 (FIG. 18A) at the distal end 202.

Figure 20:
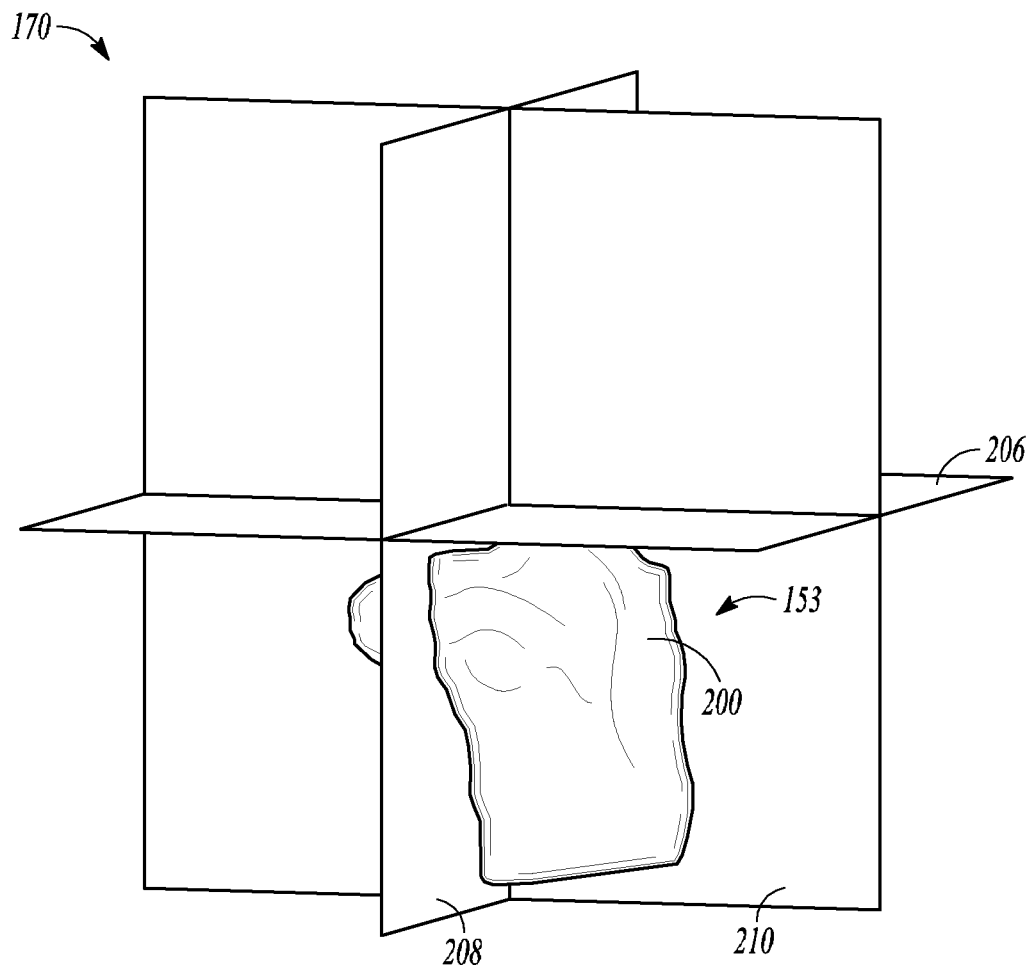
FIG. 20 is a perspective view of a proximal end of the three-dimensional tibia illustrating derived tibial anatomical reference planes in the medical coordinate system.
Figure 21A:
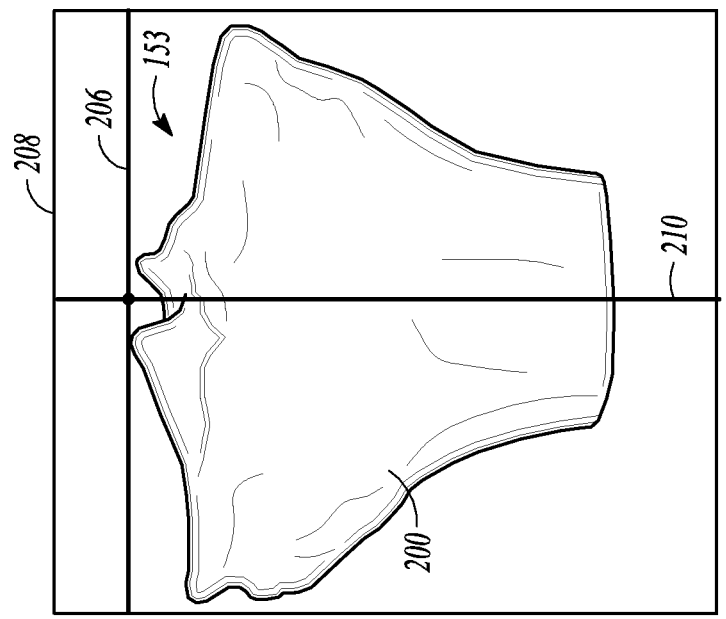
FIGS. 21A and 21B are sagittal plane and coronal plane views, respectively, illustrating the derived tibial anatomical reference planes.
Figure 21B:
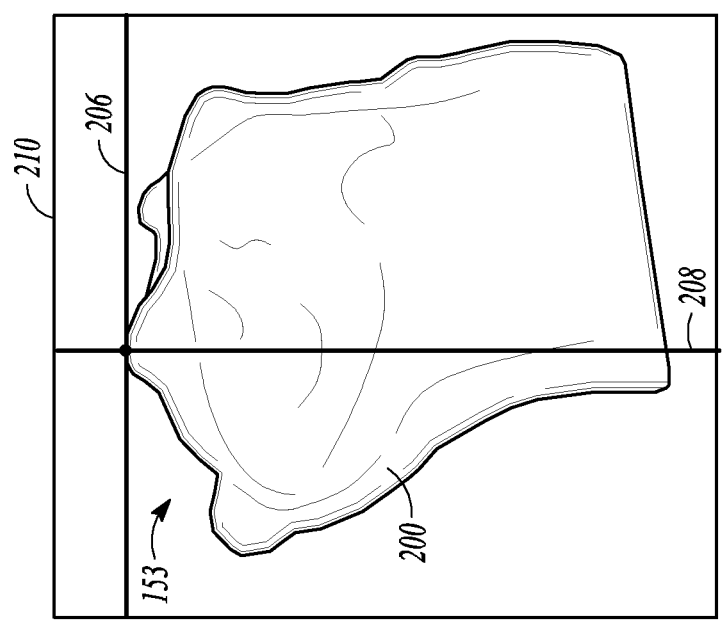

FIG. 20 is a perspective view of the proximal end 200 of the 3D tibia 153 illustrating derived anatomical reference planes in the medical coordinate system 170. Particularly, as shown in FIG. 20, the medical coordinate system 170 can include a tibial axial plane 206, a tibial coronal plane 208, and a tibial sagittal plane 210. In various examples, the tibial axial plane 206 can be defined by a plane that extends through the medial spine point 186 and the lateral spine point 188 perpendicular to the derived tibial mechanical axis 198, the tibial coronal plane 208 can be defined by a plane that extends through the derived medial-lateral axis 194 and is perpendicular to the tibial axial plane 206, and the tibial sagittal plane 210 can be defined by a plane that extends through the derived anterior-posterior axis 196 and is perpendicular to the tibial axial plane 206 and the tibial coronal plane 208. A medical coordinate system 170 that includes additional and/or different planes is also contemplated. FIGS. 21A and 21B are sagittal plane and coronal plane views, respectively, illustrating the locations of the tibial axial plane 206, the tibial coronal plane 208, and the tibial sagittal plane 210 described above.

With the femoral and tibial anatomical reference axes and reference planes in the medical coordinate system 170 identified, the pre-operative planning method can continue with a knee joint alignment process. In an example, the knee joint alignment process can begin by identifying the femoral articular surface associated with the "intact" (i.e., non-arthritic) condyle and the femoral articular surface associated with the "non-intact" (i.e., arthritic) condyle. As discussed in further detail below, the knee joint alignment process can utilize the intact condyle as a reference upon which a desired joint alignment can be simulated for surgical correction of the non-intact condyle.

Proper knee joint alignment includes adjustment of both a varus-valgus angle and a flexion-extension angle. To that end, in an example, the knee joint alignment process can continue by determining, either manually, automatically, or a combination thereof, a varus-valgus pivot point and a flexion-extension pivot point.

Figure 22B:
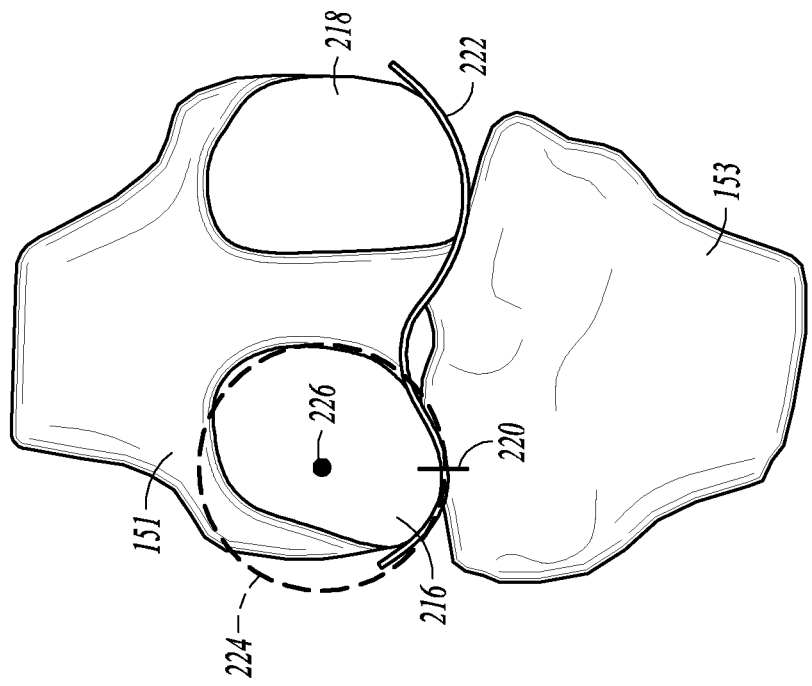
FIGS. 22A and 22B illustrate an example of a process that can be used to determine a varus-valgus pivot point in a lateral femoral condyle.
Figure 22A:
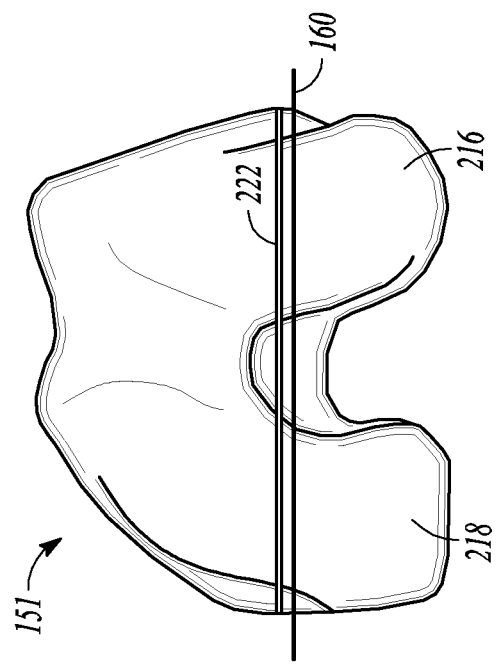

FIGS. 22A and 22B illustrate an example of a process that can be used to determine a varus-valgus pivot point in accordance with the present application. Particularly, FIG. 22A is a distal end view of the 3D femur 151 and FIG. 22B is a posterior view of the 3D femur 151 contacting the 3D tibia 153. For purposes of example only, a presumption is made that the "intact" condyle is the lateral condyle 216 and the "non-intact" condyle is the medial condyle 218. However, the process described herein can be applied in a similar manner if the "intact" condyle is the medial condyle 218.

As illustrated in FIGS. 22A and 22B, the first step in determining a varus-valgus pivot point can include, for example, identifying the contact point 220 between a distal end of the 3D femur 151 and a proximal end of the 3D tibia 151 (with the joint in extension). Then, a medial-lateral curve 222 can be projected onto the articular surface of the distal femur 151 at the approximate contact point 220 previously identified. In an example, the medial-lateral curve 222 extends along a line that is parallel to the epicondylar axis 160 (FIG. 15B). Once the medial-lateral curve 222 is projected onto the distal femoral surface, an approximating arc or circle 224 can be "best-fit" to the portion of the curve 222 along the "intact" condyle, which is the lateral condyle 216 in the present example. The approximating arc or circle 224 can be generated automatically by the computer 102 of the pre-operative planning system 100, or alternatively can be selected manually by the surgeon. Regardless of the method used to generate the approximating arc or circle 224, a center point of that arc or circle 222 represents a varus-valgus pivot point 226 about which the tibia 153 can be rotated to pre-operatively adjust and visualize the joint alignment. In an example, the varus-valgus pivot point 226 described herein extends along an axis that is generally perpendicular to the coronal plane 174 (FIG. 16).

Figure 23B:
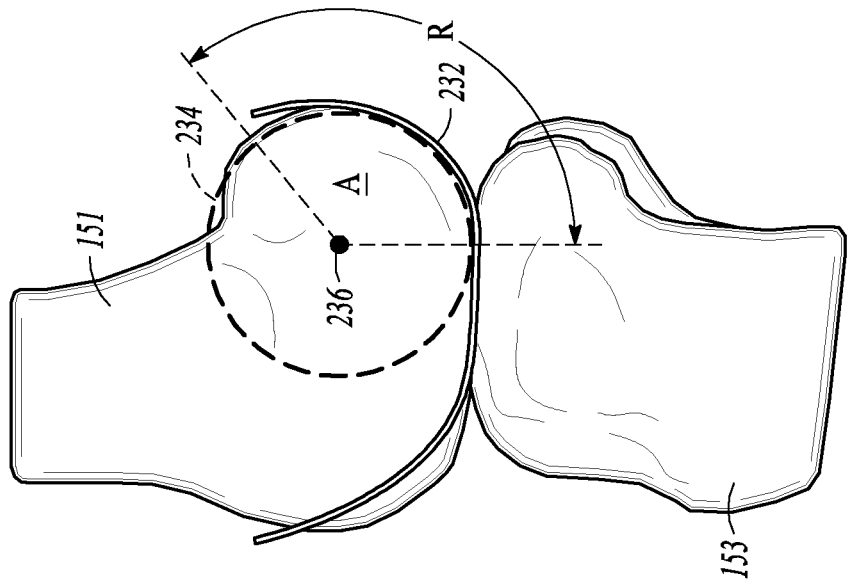
FIGS. 23A and 23B illustrate an example of a process that can be used to determine a flexion-extension pivot point in the lateral femoral condyle.
Figure 23A:
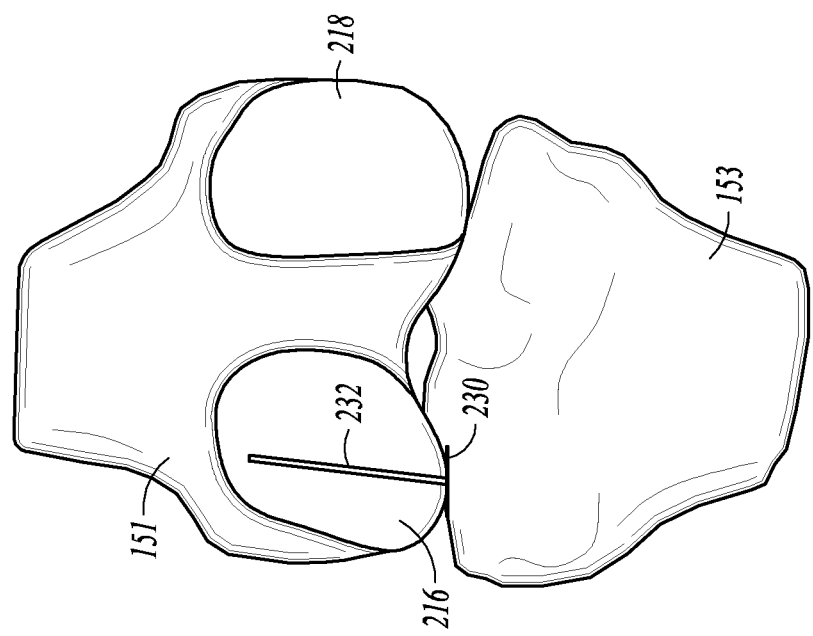

FIGS. 23A and 23B illustrate an example of a process that can be used to determine a flexion-extension pivot point in accordance with the present application. Particularly, FIG. 23A is a posterior view of the 3D femur 151 contacting the 3D tibia 153 and FIG. 23B is a sagittal view of the 3D femur 151 contacting the 3D tibia 153. As illustrated in FIGS. 23A and 23B, the first step in determining a flexion-extension pivot point can include, for example, identifying the most distal or "high" point 230 on the lateral condyle 216, or alternatively one of the most distal points on the lateral condyle 216. Then, an anterior-posterior curve 232 can be projected onto the articular surface of the distal femur 151 at the approximate distal point 230 previously identified. Once the anterior-posterior curve 232 is projected onto the distal femoral surface, an approximating arc or circle 234 can be "best-fit" to the portion of the curve 232 that lies within a specified range R defined with respect to an articular region A of the lateral condyle 216. In general, a typical range of motion for a knee joint allows for about 120 degrees of flexion. Thus, in an example, the range R defining the location where the arc or circle 234 is positioned can be about 120 degrees to generally coincide with a typical, expected range of motion. However, larger or smaller ranges can also be used.

Similar to the approximating arc or circle 224, the approximating arc or circle 234 can be generated automatically by the computer 102 of the pre-operative planning system 100, or alternatively can be selected manually by the surgeon. Regardless of the method used to generate the approximating arc or circle 234, a center point of that arc or circle 234 represents a flexion-extension pivot point 236 about which the tibia 153 can be rotated to pre-operatively adjust and visualize the limb alignment. In an example, the flexion-extension pivot point 236 described herein extends along an axis that is generally perpendicular to the sagittal plane 176 (FIG. 16).

Figure 24C:
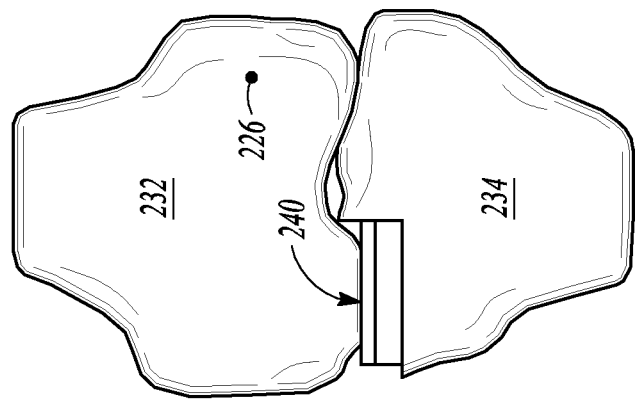
FIGS. 24A-24C illustrate a virtual knee joint alignment process using the varus-valgus pivot point.
Figure 24B:
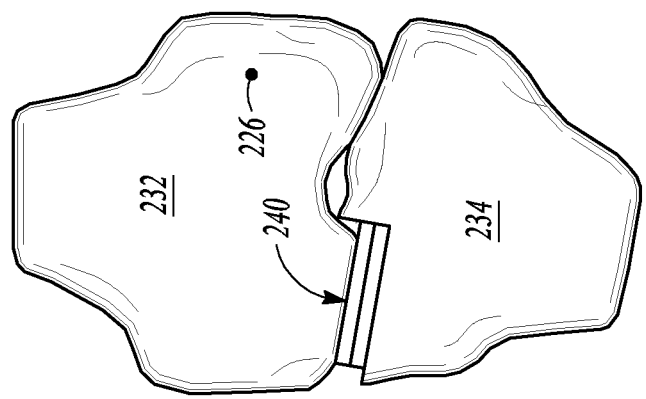
Figure 24A:
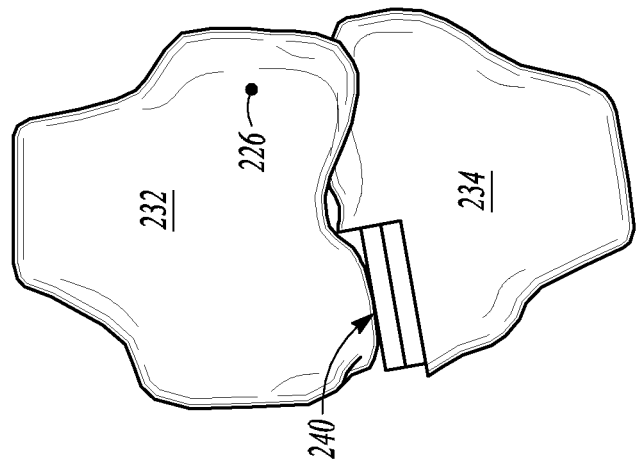

Once the varus-valgus pivot point 226 and the flexion-extension pivot point 236 have been determined, the pivot points can be used to visualize various knee joint alignments as illustrated in FIGS. 24A-24C and 25A-25C. In an example, a manipulatable 3D model 230 including a stationary femoral model 232 and a movable tibial model 234 can be displayed on the monitor 106. With reference to FIGS. 24A-24C, an anterior coronal view of the model 230 is displayed, although the model 230 can alternatively be displayed in any one or more of the other views. In an example, the surgeon can manipulate the position of the tibial model 234 with respect to the stationary femoral model 232, about the varus-valgus pivot point 226, using the controls 108 of the pre-operative planning system 100. By rotating the tibial model 234 about the varus-valgus pivot point 226, the surgeon can achieve any desired knee joint alignment, such as a valgus alignment as illustrated in FIG. 24A, a varus alignment as illustrated in FIG. 24B, or a neutral alignment as illustrated in FIG. 24C.

Figure 25C:
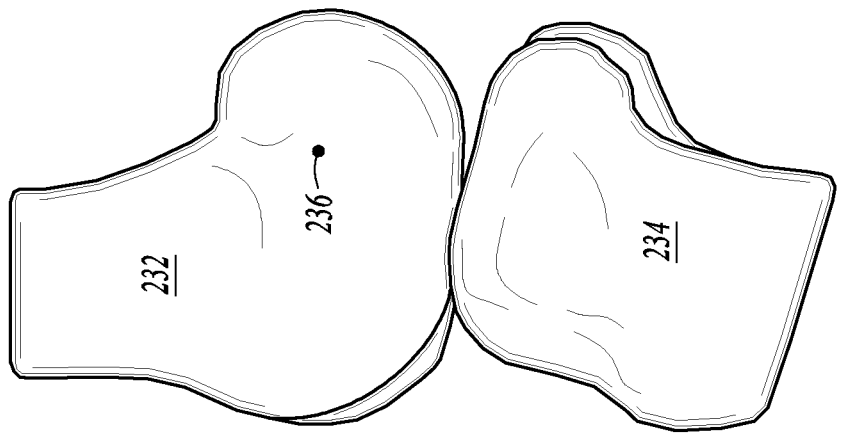
FIGS. 25A-25C illustrate a virtual knee joint alignment process using the flexion-extension pivot point.
Figure 25B:
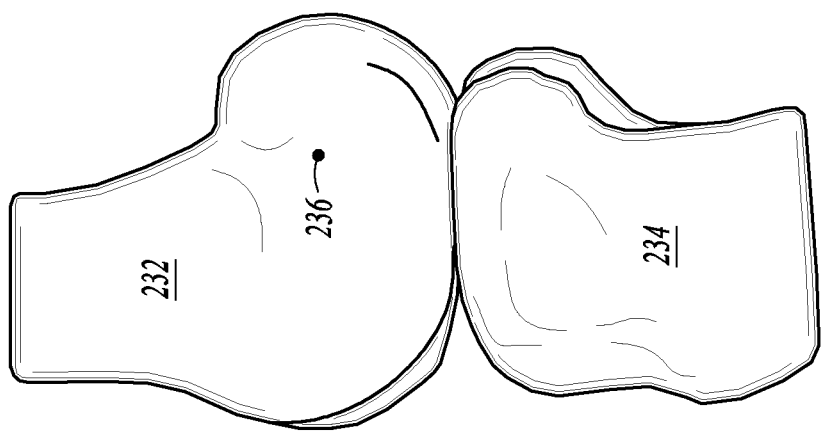
Figure 25A:
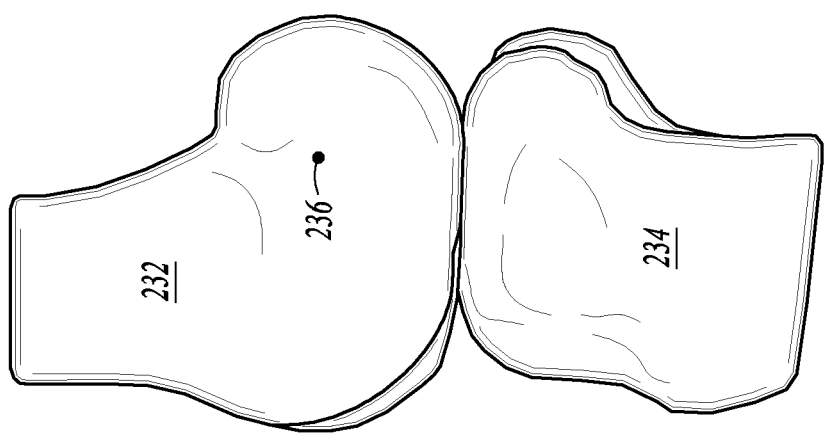

Turning next to FIGS. 25A-25C, a lateral sagittal view of the model 230 is displayed to illustrate virtual manipulation of the tibial model 234 about the flexion-extension pivot point 236. Once again, a lateral sagittal view is presented for purposes of example only, and the model 230 can alternatively or additionally be displayed in another view. In an example, the surgeon can manipulate the position of the tibial model 234 with respect to the stationary femoral model 232, about the flexion-extension pivot point 236, using the controls 108 of the pre-operative planning system 100. By rotating the tibial model 234 about the flexion-extension pivot point 236, the surgeon can achieve any desired knee joint alignment, such as full extension as illustrated in FIG. 25A, partial flexion as illustrated in FIG. 25B, or hyperextension as illustrated in FIG. 25C.

Once the model 230 has been translated to the desired alignment, a unicompartmental prosthesis can be simulated into position, such as prosthesis 240 in FIGS. 24A-24C. This simulation allows the surgeon to perform numerous preoperative activities, such as determining the appropriate thickness of the prosthesis and the position of one or more bone cuts. In an example, this data can then be used to create patient specific guides, which allow the surgeon to place the cuts in the appropriate planes and at the appropriate depths.

In the foregoing description of FIGS. 14A-25C, reference has been made to a surgeon performing the steps or processes merely for purposes of example and not limitation. Any or all of the steps or processes described above can be performed by another type of operator, such as a clinician, technician, manufacturer, or the like. In an example, the steps or processes may be carried out by a combination of several different operators.

Although the subject matter of the present patent application has been described with reference to various embodiments, workers skilled in the art will recognize that changes can be made in form and detail without departing from the scope of the invention recited in the below claims.

The claimed invention is:

1. A joint alignment method comprising:
using imaging data of at least a portion of a leg to create a leg model, the leg model including a femur having medial and lateral condyles and a tibia having a tibial plateau configured to engage the medial and lateral condyles at a knee joint, wherein one of the medial and lateral condyles is an arthritic condyle and the other one of the medial and lateral condyles is a non-arthritic condyle;
displaying an image of the leg model for manipulation by a user;
identifying a contact point between a distal end of the non-arthritic condyle and a proximal end of the tibial plateau with the knee joint in extension;
locating a first pivot point within the non-arthritic condyle, the first pivot point being defined by a center of an arc that approximates a first curvature of an outer condylar surface of the non-arthritic condyle, the first curvature extending through the contact point;
identifying a distalmost point of the non-arthritic condyle;
locating a second pivot point within the non-arthritic condyle, the second pivot point being defined by a center of an arc that approximates at least a portion of a second curvature of the outer condylar surface of the non-arthritic condyle, the second curvature extending through the distalmost point; and
rotating, in the displayed image, the tibia with respect to the femur, about one or more of the first pivot point and the second pivot point, to obtain a desired knee joint articulation in one or more of a first plane and a second plane;
wherein the first curvature is a medial-lateral curvature and the second curvature is an anterior-posterior curvature, and wherein the medial-lateral curvature extends along a plane that is parallel to a plane containing an epicondylar axis.

2. The method of claim 1, wherein the first plane is a varus-valgus plane and the second plane is a flexion-extension plane.

3. The method of claim 1, wherein the desired knee joint articulation is selected from the group consisting of a varus knee joint alignment, a valgus knee joint alignment, and a neutral knee joint alignment.

4. The method of claim 1, wherein the desired knee joint articulation is selected from the group consisting of full extension of the knee joint, flexion of the knee joint, and hyperextension of the knee joint.

5. The method of claim 1, wherein the first pivot point is a varus-valgus pivot point and the second pivot point is a flexion-extension pivot point.

6. The method of claim 1, further comprising visually displaying a prosthetic implant on the arthritic condyle after the step of rotating the tibia to obtain the desired knee joint articulation.

7. The method of claim 6, wherein the prosthetic implant indicates an implant size that is suitable for achieving the desired knee joint articulation.

8. The method of claim 1, further comprising performing the imaging using a magnetic resonance imaging system.

9. A joint alignment method comprising:
obtaining a plurality of two-dimensional images of a leg;
creating a three-dimensional leg model using the two-dimensional images, the leg model including a femur having medial and lateral condyles and a tibia having a tibial plateau configured to engage the medial and lateral condyles at a knee joint, wherein one of the medial and lateral condyles is an arthritic condyle and the other one of the medial and lateral condyles is a non-arthritic condyle;
displaying an image of the three-dimensional leg model for manipulation by a user;
identifying a contact point between a distal end of the non-arthritic condyle and a proximal end of the tibial plateau with the knee joint in extension;
locating a varus-valgus pivot point within the non-arthritic condyle, the varus-valgus pivot point being defined by a center of an arc that approximates a medial-lateral curvature of an outer condylar surface of the non-arthritic condyle, the medial-lateral curvature extending through the contact point and along a plane that is parallel to a plane containing an epicondylar axis;
identifying a distalmost point of the non-arthritic condyle;
locating a flexion-extension pivot point within the non-arthritic condyle, the flexion-extension pivot point being defined by a center of an arc that approximates at least a portion of an anterior-posterior curvature of the outer condylar surface of the non-arthritic condyle, the anterior-posterior curvature extending through the distalmost point; and
rotating, in the displayed image, the tibia with respect to the femur, about one or more of the varus-valgus pivot point and the flexion-extension pivot point, to obtain a desired knee joint articulation in one or more of a varus-valgus plane and a flexion-extension plane.

10. The method of claim 9, further comprising visually displaying a prosthetic implant on the arthritic condyle after the step of rotating the tibia to obtain the desired knee joint articulation.

11. The method of claim 10, wherein the prosthetic implant indicates an implant size that is suitable for achieving the desired knee joint articulation.

12. A pre-operative method for visualizing alignment of a joint comprising:
displaying a three-dimensional model of a knee joint, the three-dimensional model including a distal end of a femur having an arthritic condyle and a non-arthritic condyle and a proximal end of a tibia having a tibial plateau;

locating first and second pivot points within the non-arthritic condyle, wherein the first pivot point is located at a center of a medial-lateral arc that approximates a curvature of an articulation surface of the non-arthritic condyle in a first plane that is parallel to a plane containing an epicondylar axis, and wherein the second pivot point is located at a center of an anterior-posterior arc that approximates a curvature of at least a portion of the articulation surface of the non-arthritic condyle in a second plane, wherein the first plane is transverse to the second plane; and manipulating a displayed position of the arthritic condyle by rotating the tibia about the first pivot point and the second pivot point to determine a desired pre-operative alignment of the joint.

13. The method of claim 12, wherein the medial-lateral arc passes through a contact point between a distal end of the articulation surface and a proximal end of the tibial plateau.

14. The method of claim 13, wherein the anterior-posterior arc passes through a distal point on the articulation surface.

* * * * *